(12) United States Patent
Andersen et al.

(10) Patent No.: US 6,169,087 B1
(45) Date of Patent: Jan. 2, 2001

(54) MODULATORS OF PROTEIN TYROSINE PHOSPHATASES (PTPASES)

(75) Inventors: Henrik Sune Andersen; Sven Branner, both of Lyngby; Claus Bekker Jeppesen, Nivå; Niels Peter Hundahl Moeller, Copenhagen, all of (DK); Adnan M. M. Mjalli, Louisville, KY (US); Sepehr Sarshar, San Diego, CA (US)

(73) Assignees: Novo Nordisk A/S, Bagsvaerd (DK); Ontogen, Carlsbad, CA (US)

( * ) Notice: Under 35 U.S.C. 154(b), the term of this patent shall be extended for 0 days.

(21) Appl. No.: 09/157,792

(22) Filed: Sep. 21, 1998

Related U.S. Application Data

(60) Provisional application No. 60/059,598, filed on Sep. 23, 1997.

(51) Int. Cl.[7] .................... A61K 31/4985; C07D 237/00; C07D 403/02; C07D 409/02
(52) U.S. Cl. .................... 514/252.06; 514/469; 544/239; 544/235; 544/236; 549/52; 549/53; 549/54
(58) Field of Search .................... 544/235, 238, 544/239, 236; 549/52, 53, 54; 514/252, 301, 302, 312, 252.06, 469

(56) References Cited

U.S. PATENT DOCUMENTS

| | | | |
|---|---|---|---|
| 5,556,969 | * | 9/1996 | Chambers et al. .................... 540/509 |
| 5,602,171 | * | 2/1997 | Tang et al. .................... 514/455 |

FOREIGN PATENT DOCUMENTS

| | | | |
|---|---|---|---|
| 2 276 165 | * | 9/1994 | (GB). |
| WO 95/04729 | * | 2/1995 | (WO). |
| WO 95/06044 | * | 3/1995 | (WO). |
| WO 96/02525 | * | 2/1996 | (WO). |
| WO 97/28141 | * | 8/1997 | (WO). |

OTHER PUBLICATIONS

Elnagdi, Mohmed Hilmay et al., Studies with thienoazines, J.Chem. Res.,Synop.(3),130–131(1993).
Abu–Shanab, Fathi A. et al. Alkyl(oxy)pyridazinecarbonitriles as building blocks in heterocyclic synthesis,J. Chem.es. Synop. (12), 488–9(1995).
Hassan, Mohmed Ezedin, Studies on alkylheteroaromatics, Aswan Sci. Technol. Bull. 134, 33–34 (1992) also cited in CASREACT 199:28083.
Ibrahim, et al., Org. Chem. Incl. Med. Chem., vol. 36B, No. 7, pp. 612–616, (1997) CAPLUS accession No. 1997:801087.
Mohamed et al., Heterocycl. Commun., vol. 2, No. 6, pp. 539–544, (1996) Caplus accession No. 1997:98945.
Hussein et al., Al–Azhar Bull. Sci., vol. 6, No. 2, pp. 1013–1019 (1995) Caplus accession No. 1997:74415.
Al–Omran et al., Tetrahedron, vol. 52, No. 36, pp. 11915–11928 (1996) CAPLUS accession No. 1996:555042.
Al–Awadhi et al., Tetrahedron, vol. 51, No. 46, pp. 12745–62 (1995) Caplus accession No. 1995:948819.
Elghandour et al., Phosphorus Sulfur Silicon Relat. Elem., vol. 88, No. 1–4, pp. 147–153 91994) Caplus accession No. 1995:51349.
Negm et al., J. Pharm. Sci., vol. 33, No. 3–4, pp. 713–726 (1992) Caplus accession No. 1994:323441.
Hassan et al., Aswan Sci. Technol. Bull. vol. 13, pp. 33–44, (1992) Caplus accession No. 1993:428083.
Harb et al., Bull. Fac. Sci., Assiut Univ., vol. 20, No. 2, pp. 65–76 (1991) Caplus accession No. 1992:235556.
Elnagdi et al., Liebigs Ann. Chem., vol. 12, pp. 1215–1219, (1990) CAPLUS accession No. 1991:61963.
C. Jorand–Lebrun, et al., "Arylpiperazide Derivatives of Phenylpiperazines as a New Class of Potent and Selective 5–HT $_{1B}$Receptor Antagonists", (1997), Bioorganic & Medicinal Chemistry Letters, vol. 7, No.24, pp. 3183–3188.

* cited by examiner

*Primary Examiner*—Mukund J. Shah
*Assistant Examiner*—Sudhaker B. Patel
(74) *Attorney, Agent, or Firm*—Steve T. Zelson; Carol E. Rozek

(57) ABSTRACT

The present invention provides novel compounds of Formula 1 or Formula 2 and compositions thereof, methods of their use, and methods of their manufacture,

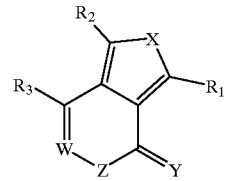

Formula 1

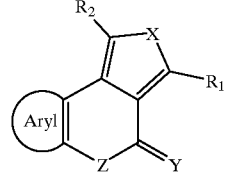

Formula 2 wherein X, Y, Z, W, $R_1$, $R_2$ and $R_3$ are defined more fully in the description. These compounds are useful in the treatment of type I diabetes, type II diabetes, impaired glucose tolerance, insulin resistance, obesity, and a number of other diseases.

20 Claims, No Drawings

MODULATORS OF PROTEIN TYROSINE PHOSPHATASES (PTPASES)

CROSS-REFERENCE TO RELATED APPLICATIONS

The present invention claims priority under 35 U.S.C. 119 of U.S. provisional application 60/059,598 filed on Sep. 23, 1997, the contents of which are fully incorporated herein by reference.

FIELD OF THE INVENTION

The present invention provides novel compounds, novel compositions, methods of their use, and methods of their manufacture, where such compounds of Formula 1 and Formula 2 are pharmacologically useful inhibitors of Protein Tyrosine Phosphatases (PTPases) such as PTP1B, CD45, PTP1C, PTPα, LAR and HePTP or the like,

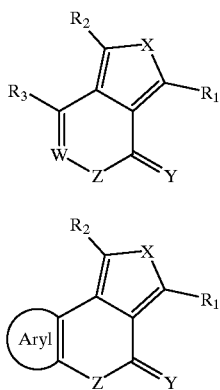

Formula 1

Formula 2 wherein W, X, Y, Z, $R_1$, $R_2$ and $R_3$ are defined more fully below. It has been found that PTPases plays a major role in the intracellular modulation and regulation of fundamental cellular signaling mechanisms involved in metabolism, growth, proliferation and differentiation (Flint et al., The EMBO J. 12:1937–46 (1993); Fischer et al, Science 253:401–6 (1991)). Overexpression or altered activity of tyrosine phosphatases can also contribute to the symptoms and progression of various diseases (Wiener, et al., J. Natl. cancer Inst. 86:372–8 (1994); Hunter and Cooper, Ann. Rev. Biochem, 54:897–930 (1985)). Furthermore, there is increasing evidence which suggests that inhibition of these PTPases may help treat certain types of diseases such as diabetes type I and II, autoimmune disease, acute and chronic inflammation, osteoporosis and various forms of cancer.

BACKGROUND OF THE INVENTION

Protein phosphorylation is now well recognized as an important mechanism utilized by cells to transduce signals during different stages of cellular function (Fischer et al, Science 253:401–6 (1991); Flint et al., The EMBO J. 12:1937–46 (1993)). There are at least two major classes of phosphatases: (1) those that dephosphorylate proteins (or peptides) that contain a phosphate group(s) on a serine or threonine moiety (termed Ser/Thr phosphatases) and (2) those that remove a phosphate group(s) from the amino acid tyrosine (termed protein tyrosine phosphatases or PTPases).

The PTPases are a family of enzymes that can be classified into two groups: a) intracellular or nontransmembrane PTPases and b) receptor-type or transmembrane PTPases.

Intracellular PTPases: Most known intracellular type PTPases contain a single conserved catalytic phosphatase domain consisting of 220–240 amino acid residues. The regions outside the PTPase domains are believed to play important roles in localizing the intracellular PTPases subcellularly (Mauro, L. J. and Dixon, J. E. TIBS 19:151–155 (1994)). The first intracellular PTPase to be purified and characterized was PTP1B which was isolated from human placenta (Tonks et al., J. Biol. Chem. 263: 6722–6730 (1988)). Shortly after, PTP1B was cloned (Charbonneau et al., Proc. Natl. Acad. Sci. USA 86: 5252–5256 (1989); Chernoff et al., Proc. Natl. Acad. Sci. USA 87: 2735–2789 (1989)). Other examples of intracellular PTPases include (1) T-cell PTPase (Cool et al. Proc. Natl. Acad. Sci. USA 86: 5257–5261 (1989)), (2) rat brain PTPase (Guan et al., Proc. Natl. Acad. Sci. USA 87:1501–1502 (1990)), (3) neuronal phosphatase STEP (Lombroso et al., Proc. Natl. Acad Sci. USA 88: 7242–7246 (1991)), (4) ezrin-domain containing PTPases: PTPMEG1 (Guet al., Proc. Natl. Acad. Sci. USA 88: 5867–57871 (1991)), PTPH1 (Yang and Tonks, Proc. Natl. Acad. Sci. USA 88: 5949–5953 (1991)), PTPD1 and PTPD2 (Møller et al., Proc. Natl. Acad. Sci. USA 91: 7477–7481 (1994)), FAP-1/BAS (Sato et al., Science 268: 411–415 (1995); Banville et al., J. Biol. Chem. 269: 22320–22327 (1994); Maekawa et al., FEBS Letters 337: 200–206 (1994)), and SH2 domain containing PTPases: PTP1C/SH-PTP1/SHP-1 (Plutzky et al, Proc. Natl. Acad. Sci. USA 89:1123–1127 (1992); Shen et al., Nature Lond. 352: 736–739 (1991)) and PTPID/Syp/SH-PTP2/SHP-2 (Vogel et al., Science 259:1611–1614 (1993); Feng et al., Science 259:1607–1611 (1993); Bastein et al., Biochem. Biophys. Res. Comm. 196:124–133 (1993)).

Low molecular weight phosphotyrosine-protein phosphatase (LMW-PTPase) shows very little sequence identity to the intracellular PTPases described above. However, this enzyme belongs to the PTPase family due to the following characteristics: (i) it possesses the PTPase active site motif: Cys-Xxx-Xxo(-XXO(-Xxx-Xxx-Arg (Cirri et al., Eur. J. Biochem. 214: 647–657 (1993)); (ii) this Cys residue forms a phospho-intermediate during the catalytic reaction similar to the situation with 'classical' PTPases (Cirri et al., supra; Chiarugi et al., FEBS Lett. 310: 9–12 (1992)); (iii) the overall folding of the molecule shows a surprising degree of similarity to that of PTP1B and Yersinia PTP (Su et al., Nature 370: 575–578 (1994)).

Receptor-type PTPases consist of a) a putative ligand-binding extracellular domain, b) a transmembrane segment, and c) an intracellular catalytic region. The structures and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains.

The first receptor-type PTPases to be identified were (1) CD45/LCA (Ralph, S. J., EMBO J. 6:1251–1257 (1987)) and (2) LAR (Streuli et al., J. Exp. Med. 168:1523–1530 (1988)) that were recognized to belong to this class of enzymes based on homology to PTP1B (Charbonneau et al., Proc. Natl. Acad. Sci. USA 86: 5252–5256 (1989)). CD45 is a family of high molecular weight glycoproteins and is one of the most abundant leukocyte cell surface glycoproteins and appears to be exclusively expressed upon cells of the hematopoietic system (Trowbridge and Thomas, Ann. Rev. Immunol. 12: 85–116 (1994)).

The identification of CD45 and LAR as members of the PTPase family was quickly followed by identification and cloning of several different members of the receptor-type PTPase group. Thus, 5 different PTPases, (3) PTPa, (4) PTPb, (5) PTPd, (6) PTPe, and (7) PTPz, were identified in one early study (Krueger et al., *EMBO J.* 9: 3241–3252 (1990)). Other examples of receptor-type PTPases include (8) PTPg (Barnea et al., *Mol. Cell. Biol*.13: 1497–1506 (1995)) which, like PTPz (Krueger and Saito, *Proc. Natl. Acad. Sci. USA* 89: 7417–7421 (1992)) contains a carbonic anhydrase-like domain in the extracellular region, (9) PTPμ (Gebbink et al., *FEBS Letters* 290: 123–130 (1991)), (10) PTPk (Jiang et al., *Mol. Cell. Biol.* 13: 2942–2951 (1993)). Based on structural differences the receptor-type PTPases may be classified into subtypes (Fischer et al., *Science* 253: 401–406 (1991)): (I) CD45; (II) LAR, PTPd, (11) PTPs ; (III) PTPb, (12) SAP-1 (Matozaki et al., *J. Biol. Chem.* 269: 2075–2081 (1994)), (13) PTP-U2/GLEPP1 (Seimiya et al., *Oncogene* 10: 1731–1738 (1995); Thomas et al., *J. Biol.Chem.* 269: 19953–19962 (1994)), and (14) DEP-1; (IV) PTPa,_PTPe. All receptor-type PTPases except Type IV contain two PTPase domains. Novel PTPases are continuously identified, and it is anticipated that more than 500 different species will be found in the human genome, i.e. close to the predicted size of the protein tyrosine kinase superfamily (Hanks and Hunter, *FASEB J.* 9: 576–596 (1995)).

PTPases are the biological counterparts to protein tyrosine kinases (PTKs). Therefore, one important function of PTPases is to control, down-regulate, the activity of PTKs. However, a more complex picture of the function of PTPases now emerges. Several studies have shown that some PTPases may actually act as positive mediators of cellular signaling. As an example, the SH2 domain-containing PTP1D seems to act as a positive mediator in insulin-stimulated Ras activation (Noguchi et al., *Mol. Cell. Biol.* 14: 6674–6682 (1994)) and of growth factor-induced mitogenic signal transduction (Xiao et al., *J. Biol. Chem.* 269: 21244–21248 (1994)), whereas the homologous PTP1C seems to act as a negative regulator of growth factor-stimulated proliferation (Bignon and Siminovitch, *Clin. Immunol. Immunopathol.* 73:168–179 (1994)). Another example of PTPases as positive regulators has been provided by studies designed to define the activation of the Src-family of tyrosine kinases. In particular, several lines of evidence indicate that CD45 is positively regulating the activation of hematopoietic cells, possibly through dephosphorylation of the C-terminal tyrosine of Fyn and Lck (Chan et al., *Annu. Rev. Immunol.*12: 555–592 (1994)).

Dual specificity protein tyrosine phosphatases (dsPTPases) define a subclass within the PTPases family that can hydrolyze phosphate from phosphortyrosine as well as from phosphor-serine/threonine. dsPTPases contain the signature sequence of PTPases: His-Cys-Axx-Xxx-Gly-Xxo-Xxx-Arg. At least three dsPTPases have been shown to dephosphorylate and inactivate extracellular signal-regulated kinase (ERKs)/mitogen-activated protein kinase (MAPK): MAPK phosphatase (CL100, 3CH134) (Charles et al, *Proc. Natl. Acad. Sci. USA* 90: 5292– 296 (1993)); PAC-1 (Ward et al., *Nature* 367: 651–654 (1994)); rVH6 Mourey et al., *J. Biol. Chem.* 271: 3795–3802 (1996)). Transcription of sPTPases are induced by different stimuli, e.g. oxidative stress or heat hock (Ishibashi et al., *J. Biol. Chem.* 269: 29897–29902 (1994); Keyse and Emslie, *Nature* 359: 644–647 (1992)). Further, they may be involved in regulation of the cell cycle: cdc25 (Millar and Russell, *Cell* 68: 407–410 (1992)); KAP (Hannon et al., *Proc. Natl. Acad. Sci. USA* 91: 1731–1735 (1994)). Interestingly, tyrosine dephosphorylation of cdc2 by a dual specific phosphatase, cdc25, is required for induction of mitosis in yeast (review by Walton and Dixon, *Annu. Rev. Biochem.* 62: 101–120 (1993)).

PTPases were originally identified and purified from cell and tissue lysates using a variety of artificial substrates and therefore their natural function of dephosphorylation was not well known. Since tyrosine phosphorylation by tyrosine kinases is usually associated with cell proliferation, cell transformation and cell differentiation, it was assumed that PTPases were also associated with these events.

This association has now been proven to be the case with many PTPases. PTP1B, a phosphatase whose structure was recently elucidated (Barford et al., Science 263:1397–1404 (1994)) has been shown to be involved in insulin-induced oocyte maturation (Flint et al., The EMBO J. 12:1937–46 (1993)) and recently it has been suggested that the overexpression of this enzyme may be involved in $p185^{c\text{-}erb\ B2}$-associated breast and ovarian cancers (Wiener, et al., J. Natl. Cancer Inst. 86:372–8 (1994); Weiner et al., Am. J. Obstet. Gynecol. 170:1177–883 (1994)). The insulin-induced oocyte maturation mechanism has been correlated with the ability of PTP1B to block activation of S6 kinase. The association with cancer is recent evidence which suggests that overexpression of PTP1B is statistically correlated with increased levels of $p185^{c\text{-}erb\ B2}$ in ovarian and breast cancer. The role of PTP1B in the etiology and progression of the disease has not yet been elucidated. Inhibitors of PTP1B may therefore help clarify the role of PTP1B in cancer and in some cases provide therapeutic treatment for certain forms of cancer.

The activity of a number of other newly discussed phosphatases are currently under investigation. Two of these: PTP1C and Syp/PTP1DISHPTP2/PTP2C have recently been implicated in the activation of Platelet Derived Growth Factor and Epidermal Growth Factor induced responses (Li et al., Mole. Cell. Biol. 14:509–17 (1994)). Since both growth factors are involved in normal cell processing as well as disease states such as cancer and artherosclerosis, it is hypothesized that inhibitors of these phosphatases would also show therapeutic efficacy. Accordingly, the compounds of the present invention which exhibit inhibitory activity against various PTPases, are indicated in the treatment or management of the foregoing diseases.

PTPases: the insulin receptor signaling pathway/diabetes

Insulin is an important regulator of different metabolic processes and plays a key role in the control of blood glucose. Defects related to its synthesis or signaling lead to diabetes mellitus. Binding of insulin to its receptor causes rapid (auto)phosphorylation of several tyrosine residues in the intracellular part of the b-subunit. Three closely positioned tyrosine residues (the tyrosine-1150 domain) must all be phosphorylated to obtain full activity of the insulin receptor tyrosine kinase (IRTK) which transmits the signal further downstream by tyrosine phosphorylation of other cellular substrates, including insulin receptor substrate-1 (IRS-1) (Wilden et al., *J. Biol. Chem.* 267: 16660–16668 (1992); Myers and White, *Diabetes* 42: 643–650 (1993); Lee and Pilch, *Am. J. Physiol.* 266: C319–C334 (1994); White et al., *J. Biol. Chem.* 263: 2969–2980 (1988)). The structural basis for the function of the tyrosine-triplet has been provided by recent X-ray crystallographic studies of IRTK that showed tyrosine-1150 to be autoinhibitory in its unphosphorylated state (Hubbard et al., *Nature* 372: 746–754 (1994)).

Several studies clearly indicate that the activity of the auto-phosphorylated IRTK can be reversed by dephosphorylation in vitro (reviewed in Goldstein, *Receptor* 3: 1–15 (1993); Mooney and Anderson, *J. Biol.Chem.* 264: 6850–6857 (1989)), with the tri-phosphorylated tyrosine- 1150 domain being the most sensitive target for protein-tyrosine phosphatases (PTPases) as compared to the di- and mono- phosphorylated forms (King et al., *Biochem. J.* 275: 413–418 (1991)). It is, therefore, tempting to speculate that this tyrosine-triplet functions as a control switch of IRTK activity. Indeed, the IRTK appears to be tightly regulated by PTP-mediated dephosphorylation in vivo (Khan et al., *J. Biol. Chem.* 264: 12931–12940 (1989); Faure et al., *J. Biol. Chem.* 267: 11215–11221 (1992); Rothenberg et al., *J. Biol. Chem.* 266: 8302–8311 (1991)). The intimate coupling of PTPases to the insulin signaling pathway is further evidenced by the finding that insulin differentially regulates PTPase activity in rat hepatoma cells (Meyerovitch et al., *Biochemistry* 31: 10338–10344 (1992)) and in livers from alloxan diabetic rats (Boylan et al., *J. Clin. Invest.* 90: 174–179 (1992)).

Relatively little is known about the identity of the PTPases involved in IRTK regulation. However, the existence of PTPases with activity towards the insulin receptor can be demonstrated as indicated above. Further, when the strong PTPase-inhibitor pervanadate is added to whole cells an almost full insulin response can be obtained in adipocytes (Fantus et al., *Biochemistry* 28: 8864–8871 (1989); Eriksson et al., *Diabetologia* 39: 235–242 (1995)) and skeletal muscle (Leighton et al., *Biochem. J.* 276: 289–292 (1991)). In addition, recent studies show that a new class of peroxovanadium compounds act as potent hypoglycemic compounds in vivo (Posner et al.,supra). Two of these compounds were demonstrated to be more potent inhibitors of dephosphorylation of the insulin receptor than of the EGF-receptor.

It was recently found that the ubiquitously expressed SH2 domain containing PTPase, PTP1D (Vogel et al., 1993, supra), associates with and dephosphorylates IRS-1, but apparently not the IR itself (Kuhné et al.,*J. Biol. Chem.* 268: 11479–11481 (1993); (Kuhné et al., *J. Biol. Chem.* 269:15833–15837 (1994)).

Previous studies suggest that the PTPases responsible for IRTK regulation belong to the class of membrane-associated (Faure et al., *J. Biol. Chem.* 267:11215–11221 (1992)) and glycosylated molecules (Häring et al., *Biochemistry* 23: 3298–3306 (1984); Sale, *Adv. Prot. Phosphatases* 6:159–186 (1991)). Hashimoto et al. have proposed that LAR might play a role in the physiological regulation of insulin receptors in intact cells (Hashimoto et al., *J. Biol.Chem.* 267: 13811–13814 (1992)). Their conclusion was reached by comparing the rate of dephosphorylationli-nactivation of purified IR using recombinant PTP1B as well as the cytoplasmic domains of LAR and PTPa. Antisense inhibition was recently used to study the effect of LAR on insulin signaling in a rat hepatoma cell line (Kulas et al., *J. Biol. Chem.* 270: 2435–2438 (1995)). A suppression of LAR protein levels by about 60 percent was paralleled by an approximately 150 percent increase in insulin-induced autophosphorylation. However, only a modest 35 percent increase in IRTK activity was observed, whereas the insulin-dependent phosphatidylinositol 3-kinase (PI 3-kinase) activity was significantly increased by 350 percent. Reduced LAR levels did not alter the basal level of IRTK tyrosine phosphorylation or activity. The authors speculate that LAR could specifically dephosphorylate tyrosine residues that are critical for PI 3-kinase activation either on the insulin receptor itself or on a downstream substrate. While previous reports indicate a role of PTPa in signal transduction through src activation (Zheng et al., *Nature* 359: 336–339 (1992); den Hertog et al., *EMBO J.* 12: 3789–3798 (1993)) and interaction with GRB-2 (den Hertog et al., *EMBO J.* 13: 3020–3032 (1994); Su et a., *J. Biol. Chem.* 269: 18731–18734 (1994)), a recent study suggests a function for this phosphatase and its close relative PTPe as negative regulators of the insulin receptor signal (Møller et al., 1995 supra). This study also indicates that receptor-like PTPases play a significant role in regulating the IRTK, whereas intracellular PTPases seem to have little, if any, activity towards the insulin receptor. While it appears that the target of the negative regulatory activity of PTPases a and e is the receptor itself, the downmodulating effect of the intracellular TC-PTP seems to be due to a downstream function in the IR-activated signal. Although PTP1B and TC-PTP are closely related, PTP1B had only little influence on the phosphorylation pattern of insulin-treated cells. Both PTPases have distinct structural features that determine their subcellular localization and thereby their access to defined cellular substrates (Frangione et al., *Cell* 68: 545–560 (1992); Faure and Posner, *Glia* 9: 311–314 (1993)). Therefore, the lack of activity of PTP1B and TC-PTP towards the IRTK may, at least in part, be explained by the fact that they do not co-localize with the activated insulin receptor. In support of this view, PTP1B and TC-PTP have been excluded as candidates for the IR-associated PTPases in hepatocytes based on subcellular localization studies (Faure et al., *J. Biol. Chem.* 267: 11215–11221 (1992)).

The transmembrane PTPase CD45, which is believed to be hematopoietic cell-specific, was in a recent study found to negatively regulate the insulin receptor tyrosine kinase in the human multiple myeloma cell line U266 (Kulas et al., *J. Biol.Chem.* 271: 755–760 (1996)).

PTPases: somatostatin

Somatostatin inhibits several biological functions including cellular proliferation (Lamberts et al., *Molec. Endocrinol.* 8: 1289–1297 (1994)). While part of the antiproliferative activities of somatostatin are secondary to its inhibition of hormone and growth factor secretion (e.g. growth hormone and epidermal growth factor), other antiproliferative effects of somatostatin are due to a direct effect on the target cells. As an example, somatostatin analogs inhibit the growth of pancreatic cancer presumably via stimulation of a single PTPase, or a subset of PTPases, rather than a general activation of PTPase levels in the cells (Liebow et al., *Proc. Natl. Acad. Sci. USA* 86: 2003–2007 (1989); Colas et al., *Eur. J. Biochem.* 207: 1017–1024 (1992)). In a recent study it was found that somatostatin stimulation of somatostatin receptors SSTR1, but not SSTR2, stably expressed in CHO-K1 cells can stimulate PTPase activity and that this stimulation is pertussis toxin-sensitive. Whether the inhibitory effect of somatostatin on hormone and growth factor secretion is caused by a similar stimulation of PTPase activity in hormone producing cells remains to be determined.

PTPases: the immune system/autoimmunity

Several studies suggest that the receptor-type PTPase CD45 plays a critical role not only for initiation of T cell activation, but also for maintaining the T cell receptor-mediated signaling cascade. These studies are reviewed in: (Weiss A., *Ann. Rev. Genet* 25: 487–510 (1991); Chan et al., *Annu. Rev. Immunol* 12: 555–592 (1994); Trowbridge and Thomas, *Annu. Rev. Immunol.* 12: 85–116 (1994)). CD45 is one of the most abundant of the cell surface glycoproteins and is expressed exclusively on hemopoetic cells. In T cells, it has been shown that CD45 is one of the critical components of the signal transduction machinery of lymphocytes. In particular, evidence has suggested that CD45 phosphatase plays a pivotal role in antigen-stimulated proliferation of T lymphocytes after an antigen has bound to the T cell receptor (Trowbridge, Ann. Rev. immunol, 12:85–116 (1994)). Several studies suggest that the PTPase activity of CD45 plays a role in the activation of Lck, a lymphocyte-specific member of the Src family protein-tyrosine kinase (Mustelin etal., Proc. Natl. Acad. Sci. USA 86: 6302–6306 (1989); Ostergaard et al., Proc. Natl. Acad. Sci. USA 86: 8959–8963 (1989)). These authors hypothesized that the phosphatase activity of CD45 activates Lck by dephosphorylation of a C-terminal tyrosine residue, which may, in turn, be related to T-cell activation. In a recent study it was found that recombinant p56lck specifically associates with recombinant CD45 cytoplasmic domain protein, but not to the cytoplasmic domain of the related PTPa (Ng et al., J. Biol. Chem. 271: 1295–1300 (1996)). The p56lck-CD45 interaction seems to be mediated via a nonconventional SH2 domain interaction not requiring phosphotyrosine. In immature B cells, another member of the Src family protein-tyrosine kinases, Fyn, seems to be a selective substrate for CD45 compared to Lck and Syk (Katagiri et al., J. Biol. Chem. 270: 27987–27990 (1995)).

Studies using transgenic mice with a mutation for the CD45-exon6 exhibited lacked mature T cells. These mice did not respond to an antigenic challenge with the typical T cell mediated response (Kishihara et al., Cell 74:143–56 (1993)). Inhibitors of CD45 phosphatase would therefore be very effective therapeutic agents in conditions that are associated with autoimmune disease.

CD45 has also been shown to be essential for the antibody mediated degranulation of mast cells (Berger et al., J. Exp. Med. 180:471–6 (1994)). These studies were also done with mice that were CD45-deficient. In this case, an IgE-mediated degranulation was demonstrated in wild type but not CD45-deficient T cells from mice. These data suggest that CD45 inhibitors could also play a role in the symptomatic or therapeutic treatment of allergic disorders.

Another recently discovered PTPase, an inducible lymphoid-specific protein tyrosine phosphatase (HePTP) has also been implicated in the immune response. This phosphatase is expressed in both resting T and B lymphocytes, but not non-hemopoetic cells. Upon stimulation of these cells, mRNA levels from the HePTP gene increase 10–15 fold (Zanke et al., Eur. J. Immunol. 22:235–239 (1992)). In both T and B cells HePTP may function during sustained stimulation to modulate the immune response through dephosphorylation of specific residues. Its exact role, however remains to be defined.

Likewise, the hematopoietic cell specific PTP1C seems to act as a negative regulator and play an essential role in immune cell development. In accordance with the above-mentioned important function of CD45, HePTP and PTP1C, selective PTPase inhibitors may be attractive drug candidates both as immunosuppressors and as immunostimulants. One recent study illustrates the potential of PTPase inhibitors as immunmodulators by demonstrating the capacity of the vanadium-based PTPase inhibitor, BMLOV, to induce apparent B cell selective apoptosis compared to T cells (Schieven et al., J. Biol. Chem. 270: 20824–20831 (1995)).

PTPases: cell-cell interactions/cancer

Focal adhesion plaques, an in vitro phenomenon in which specific contact points are formed when fibroblasts grow on appropriate substrates, seem to mimic, at least in part, cells and their natural surroundings. Several focal adhesion proteins are phosphorylated on tyrosine residues when fibroblasts adhere to and spread on extracellular matrix (Gumbiner, Neuron 11, 551–564 (1993)). However, aberrant tyrosine phosphorylation of these proteins can lead to cellular transformation. The intimate association between PTPases and focal adhesions is supported by the finding of several intracellular PTPases with ezrin-like N-terminal domains, e.g. PTPMEGI (Gu et al., Proc. Natl. Acad. Sci. USA 88: 5867–5871 (1991)), PTPH1 (Yang and Tonks, Proc. Natl. Acad. Sci. USA 88: 5949–5953 (1991)) and PTPD1 (Møller et al., Proc. Natl. Acad. Sci. USA 91: 7477–7481 (1994)). The ezrin-like domain show similarity to several proteins that are believed to act as links between the cell membrane and the cytoskeleton. PTPD1 was found to be phosphorylated by and associated with c-src in vitro and is hypothesized to be involved in the regulation of phosphorylation of focal adhesions (Møller et al., supra).

PTPases may oppose the action of tyrosine kinases, including those responsible for phosphorylation of focal adhesion proteins, and may therefore function as natural inhibitors of transformation. TC-PTP, and especially the truncated form of this enzyme (Cool et al., Proc. Natl. Acad. Sci. USA 87: 7280–7284 (1990)), can inhibit the transforming activity of v-erb and v-fms (Lammers et al., J. Biol. Chem. 268: 22456–22462 (1993); Zander et al., Orcogene 8: 1175–1182 (1993)). Moreover, it was found that transformation by the oncogenic form of the HER2/neu gene was suppressed in NIH 3T3 fribroblasts overexpressing PTP1B (Brown-Shimer et al., Cancer Res. 52: 478–482 (1992)).

The expression level of PTP1B was found to be increased in a mammary cell line transformed with neu (Zhay et al., Cancer Res. 53: 2272–2278 (1993)). The intimate relationship between tyrosine kinases and PTPases in the development of cancer is further evidenced by the recent finding that PTPe is highly expressed in murine mammary tumors in transgenic mice over-expressing c-neu and v-Ha-ras, but not c-myc or int-2 (Elson and Leder, J. Biol. Chem. 270:26116–26122 (1995)). Further, the human gene encoding PTPg was mapped to 3p21, a chromosomal region which is frequently deleted in renal and lung carcinomas (LaForgia et a[., Proc. Natl. Acad. Sci. USA 88: 5036–5040 (1991)).

In this context, it seems significant that PTPases appear to be involved in controlling the growth of fibroblasts. In a recent study it was found that Swiss 3T3 cells harvested at high density contain a membrane-associated PTPase whose activity on an average is 8-fold higher than that of cells harvested at low or medium density (Pallen and Tong, Proc. Natl. Acad. Sci. USA 88: 6996–7000 (1991)). It was hypothesized by the authors that density-dependent inhibition of cell growth involves the regulated elevation of the activity of the PTPase(s) in question. In accordance with this view, a novel membrane-bound, receptor-type PTPase, DEP-1, showed enhanced (>=10-fold) expression levels with increasing cell density of WI-38 human embryonic lung fibroblasts and in the AG1518 fibroblast cell line (Östman et al., Proc. Natl. Acad. Sci. USA 91: 9680–9684 (1994)).

Two closely related receptor-type PTPases, PTPk and PTPμ, can mediate homophilic cell-cell interaction when expressed in non-adherent insect cells, suggesting that these PTPases might have a normal physiological function in cell-to-cell signaling (Gebbink et at., J. Biol.Chem. 268: 16101–16104 (1993); Brady-Kalnay et al.,J. Cell Biol. 122: 961–972 (1993); Sap et al., Mol. Cell. Biol. 14: 1–9 (1994)). Interestingly, PTPk and PTPμ do not interact with each other, despite their structural similarity (Zondag et al., J. Biol.Chem. 270: 14247–14250 (1995)). From the studies described above it is apparent that PTPases may play an important role in regulating normal cell growth. However, as pointed out above, recent studies indicate that PTPases may also function as positive mediators of intracellular signaling and thereby induce or enhance mitogenic responses. Increased activity of certain PTPases might therefore result in cellular transformation and tumor formation. Indeed, in one study over-expression of PTPα was found to lead to transformation of rat embryo fibroblasts (Zheng, supra). In addition, a novel PTP, SAP-1, was found to be highly expressed in pancreatic and colorectal cancer cells. SAP-1 is mapped to chromosome 19 region q13.4 and might be related to carcinoembryonic antigen mapped to 19q 13.2 (Uchida et al., *J. Biol.Chem.* 269: 12220–12228 (1994)). Further, the dsPTPase, cdc25, dephosphorylates cdc2 at Thr14/Tyr-15 and thereby functions as positive regulator of mitosis (reviewed by Hunter, *Cell* 80: 225–236 (1995)). Inhibitors of specific PTPases are therefore likely to be of significant therapeutic value in the treatment of certain forms of cancer.

PTPases: platelet aggregation

Recent studies indicate that PTPases are centrally involved in platelet aggregation. Agonist-induced platelet activation results in calpain-catalyzed cleavage of PTP1B with a concomitant 2-fold stimulation of PTPase activity (Frangioni et al., *EMBO J.* 12:48434856 (1993)). The cleavage of PTP1B leads to subcellular relocation of the enzyme and correlates with the transition from reversible to irreversible platelet aggregation in platelet-rich plasma. In addition, the SH2 domain containing PTPase, PTP1C/SH-PTP1, was found to translocate to the cytoskeleton in platelets after thrombin stimulation in an aggregation-dependent manner (Li et al., *FEBS Lett.* 343: 89–93 (1994)).

Although some details in the above two studies were recently questioned there is over-all agreement that PTP1B and PTP1C play significant functional roles in platelet aggregation (Ezumi et al., *J. Biol. Chem.* 270:11927–11934 (1995)). In accordance with these observations, treatment of platelets with the PTPase inhibitor pervanadate leads to significant increase in tyrosine phosphorylation, secretion and aggregation (Pumiglia et al., *Biochem. J.* 286: 441–449 (1992)).

PTPases: osteoporosis

The rate of bone formation is determined by the number and the activity of osteoblasts, which in term are determined by the rate of proliferation and differentiation of osteoblas progenitor cells, respectively. Histomorphometric studies indicate that the osteoblast number is the primary determinant of the rate of bone formation in humans (Gruber et al., *Mineral Electrolyte Metab.* 12: 246–254 (1987); reviewed in Lau et al., *Biochem. J.* 257: 23–36 (1989)). Acid phosphatases/PTPases may be involved in negative regulation of osteoblast proliferation. Thus, fluoride, which has phosphatase inhibitory activity, has been found to increase spinal bone density in osteoporotics by increasing osteoblast proliferation (Lau et al., supra). Consistent with this observation, an osteoblastic acid phosphatase with PTPase activity was found to be highly sensitive to mitogenic concentrations of fluoride (Lau et al., *J. Biol. Chem.* 260: 4653–4660 (1985); Lau et al., *J. Biol. Chem.* 262: 1389–1397 (1987); Lau et al., *Adv. Protein Phosphatases* 4:165–198 (1987)). Interestingly, it was recently found that the level of membrane-bound PTPase activity was increased dramatically when the osteoblast-like cell line UMR 106.06 was grown on collagen type-l matrix compared to uncoated tissue culture plates. Since a significant increase in PTPase activity was observed in density-dependent growth arrested fibroblasts (Pallen and Tong, *Proc. Natl. Acad. Sci.* 88: 6996–7000 (1991)), it might be speculated that the increased PTPase activity directly inhibits cell growth. The mitogenic action of fluoride and other phosphatase inhibitors (molybdate and vanadate) may thus be explained by their inhibition of acid phosphatases/PTPases that negatively regulate the cell proliferation of osteoblasts. The complex nature of the involvement of PTPases in bone formation is further suggested by the recent identification of a novel parathyroid regulated, receptor-like PTPase, OST-PTP, expressed in bone and testis (Mauro et al., *J. Biol. Chem.* 269: 30659–30667 (1994)). OST-PTP is up-regulated following differentiation and matrix formation of primary osteoblasts and subsequently down-regulated in the osteoblasts which are actively mineralizing bone in culture. It may be hypothesized that PTPase inhibitors may prevent differentiation via inhibition of OST-PTP or other PTPases thereby leading to continued proliferation. This would be in agreement with the above-mentioned effects of fluoride and the observation that the tyrosine phosphatase inhibitor orthovanadate appears to enhance osteoblast proliferation and matrix formation (Lau et al., *Endocrinology* 116: 2463–2468 (1988)). In addition, it was recently observed that vanadate, vanadyl and pervanadate all increased the growth of the osteoblast-like cell line UMR106. Vanadyl and pervanadate were stronger stimulators of cell growth than vanadate. Only vanadate was able to regulate the cell differentiation as measured by cell alkaline phosphatase activity (Cortizo et al., *Mol. Cell. Biochem.* 145: 97–102 (1995)).

PTPases: microorganisms

Dixon and coworkers have called attention to the fact that PTPases may be a key element in the pathogenic properties of Yersinia (reviewed in Clemens et al. *Molecular Microbiology* 5: 2617–2620 (1991)). This finding was rather surprising since tyrosine phosphate is thought to be absent in bacteria. The genus Yersinia comprises 3 species: *Y. pestis* (responsible for the bubonic plague), *Y. pseudoturberculosis* and *Y. enterocolitica* (causing enteritis and mesenteric lymphadenitis). Interestingly, a dual-specificity phosphatase, VH1, has been identified in Vaccinia virus (Guan et al., *Nature* 350: 359–263 (1991)). These observations indicate that PTPases may play critical roles in microbial and parasitic infections, and they further point to PTPase inhibitors as a novel, putative treatment principle of infectious diseases.

DESCRIPTION OF THE INVENTION

The present invention relates to compounds of Formula 1 and Formula 2, wherein W, X, Y, Z, $R_1$, $R_2$, $R_3$ are defined below.

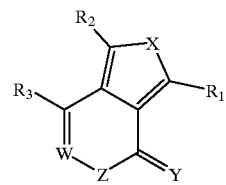

Formula 1

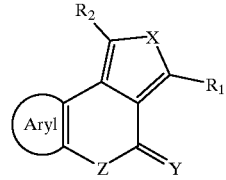

Formula 2

In the above Formula 1 and Formula 2,

X is O, NH, S, SO or $SO_2$;

Y is O or S;

$R_1$ is $NO_2$, $NH_2$ or $NHR_4$ wherein $R_4$ is $SO_2CF_3$, $C_1$–$C_6$alkyl or $C_1$–$C_6$alkylaryl, wherein the alkyl and aryl groups may be optionally substituted;

$R_2$ is hydrogen, nitro, halo, cyano, $C_1$–$C_6$alkyl, aryl, aryl$C_1$–$C_6$alkyl, COOH, carboxy$C_1$–$C_6$alkyl, $C_1$–$C_6$alkyloxycarbonyl, aryloxycarbonyl, aryl$C_1$–$C_6$alkyloxycarbonyl or CONR$_6$R$_7$, wherein R$_6$ and R$_7$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein the alkyl and aryl groups are optionally substituted; or $R_6$ and $R_7$ are taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1$–$C_6$alkyl, aryl, aryl$C_1$–$C_6$alkyl, hydroxy, $C_1$–$C_6$alkyloxy, aryl$C_1$–$C_6$alkyloxy, $C_1$–$C_6$alkyloxy$C_1$–$C_6$alkyl, NR$_9$R$_{10}$ or $C_1$–$C_6$alkylamino$C_1$–$C_6$alkyl, wherein R$_9$ and R$_{10}$ are independently selected from hydrogen, $C_1$–$C_6$alkyl, aryl, aryl$C_1$–$C_6$alkyl, $C_1$–$C_6$alkyl-carbonyl, arylcarbonyl, aryl$C_1$–$C_6$alkylcarbonyl, $C_1$–$C_6$alkyl-carboxy or aryl$C_1$–$C_6$alkylcarboxy wherein the alkyl and aryl groups are optionally substituted; or $R_6$ and $R_7$ are independently a saturated or partial saturated cyclic 5,6 or 7 membered amine or lactam;

$R_3$ is hydrogen, cyano, hydroxy, thiol, $C_1$–$C_6$alkylthio, SO$C_1$–$C_6$alkyl, SO$_2$$C_1$–$C_6$alkyl, COOR$_5$, $C_1$–$C_6$alkyl, $C_1$–$C_6$alkyloxy, NR$_6$R$_7$, aryl, aryl$C_1$–$C_6$alkyl, $C_1$–$C_6$alkyloxycarbonyl$C_1$–$C_6$alkyl, aryl$C_1$–$C_6$alkyloxycarbonyl$C_1$–$C_6$alkyl, CONR$_6$R$_7$, -carbonylNR$_6$$C_1$–$C_6$alkylCOR$_8$, wherein R$_5$ is selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy, $C_1$–$C_6$alkyloxycarbonyl$C_1$–$C_6$alkyl, aryl$C_1$–$C_6$alkyloxy-carbonyl$C_1$–$C_6$alkyl; wherein the alkyl and aryl groups are optionally substituted as defined below and R$_6$ and R$_7$ are defined as above;

$R_8$ is hydroxy, $C_1$–$C_6$alkyl, aryl, aryl$C_1$–$C_6$alkyl, $C_1$–$C_6$alkyloxy, aryloxy, aryl$C_1$–$C_6$alkyloxy or NR$_6$R$_7$; wherein R$_6$ and R$_7$ are defined as above;

W is N and Z is NR$_{11}$ or CR$_{11}$R$_{12}$;

or

W is CR$_{11}$ and Z is O or NR$_{11}$;

wherein R$_{11}$ and R$_{12}$ are independently selected from hydrogen, $C_1$–$C_6$alkyl, aryl, aryl$C_1$–$C_6$alkyl, wherein the alkyl and aryl groups are optionally substituted;

In formula 2; the aryl group is an unsubstituted, mono-, di- or trisubstituted monocyclic, polycyclic, biaryl or heterocyclic aromatic fused group optionally substituted as outlined below under the definition section.

Definitions

As used herein, the term "attached" or "-" (e.g. —COR$_8$ which indicates that the carbonyl is attached to the scaffold) signifies a stable covalent bond, certain preferred points of attachment being apparent to those skilled in the art.

The terms "halogen" or "halo" include fluorine, chlorine, bromine, and iodine.

The term "alkyl" includes $C_1$–$C_6$ straight chain saturated and $C_2$–$C_6$ unsaturated aliphatic hydrocarbon groups, $C_1$–$C_6$ branched saturated and $C_2$–$C_6$ unsaturated aliphatic hydrocarbon groups, $C_3$–$C_6$ cyclic saturated and $C_5$–$C_6$ unsaturated aliphatic hydrocarbon groups, and $C_1$–$C_6$ straight chain or branched saturated and $C_2$–$C_6$ straight chain or branched unsaturated aliphatic hydrocarbon groups substituted with $C_3$–$C_6$ cyclic saturated and unsaturated aliphatic hydrocarbon groups having the specified number of carbon atoms.

For example, this definition shall include but is not limited to methyl (Me), ethyl (Et), propyl (Pr), butyl (Bu), pentyl, hexyl, heptyl, ethenyl, propenyl, butenyl, penentyl, hexenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cyclopentenyl, cyclohexenyl, methylcyclopropyl, ethylcyclohexenyl, butenylcyclopentyl, and the like.

The term "substituted alkyl" represents an alkyl group as defined above wherein the substitutents are independently selected from halo, cyano, nitro, trihalomethyl, carbamoyl, hydroxy, COOR$_5$, $C_1$–$C_6$alkyloxy, aryloxy, aryl$C_1$–$C_6$alkyloxy, thio, $C_1$–$C_6$alkylthio, arylthio, aryl$C_1$–$C_6$alkylthio, NR$_6$R$_7$, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$alkylcarbonyl, $C_1$–$C_6$alkylcarboxy, aryl$C_1$–$C_6$alkylcarboxy, $C_1$–$C_6$alkylcarbonylamino, -$C_1$–$C_6$alkyl-aminoCOR$_8$, aryl$C_1$–$C_6$alkylcarbonylamino, tetrahydrofuryl, morpholinyl, piperazinyl, hydroxypyranyl, —COR$_8$, —CONR$_6$R$_7$, -$C_1$–$C_6$alkylCONR$_6$R$_7$ wherein R$_5$, R$_6$, R$_7$ and R$_8$ are defined as above.

The term "alkyloxy" (e.g. methoxy, ethoxy, propyloxy, allyloxy, cyclohexyloxy) represents an "alkyl" group as defined above having the indicated number of carbon atoms attached through an oxygen bridge. The term "alkyloxyalkyl" represents an "alkyloxy" group attached through an alkyl group as defined above having the indicated number of carbon atoms.

The term "aryloxy" (e.g. phenoxy, naphthyloxy and the like) represents an aryl group as defined below attached through an oxygen bridge. The term "arylalkyloxy" (e.g. phenethyloxy, naphthylmethyloxy and the like) represents an "arylalkyl" group as defined below attached through an oxygen bridge.

The term "arylalkyloxyalkyl" represents an "arylalkyloxy" group as defined above attached through an "alkyl" group defined above having the indicated number of carbon atoms.

The term "arylthio" (e.g. phenylthio, naphthylthio and the like) represents an "aryl" group as defined below attached through an sulfur bridge.

The term "alkyloxycarbonyl" (e.g. methylformiat, ethylformiat and the like) represents an "alkyloxy" group as defined above attached through a carbonyl group.

The term "aryloxycarbonyl" (e.g. phenylformiat, 2-thiazolylformiat and the like) represents an "aryloxy" group as defined above attached through a carbonyl group.

The term "arylalkyloxycarbonyl" (e.g. benzylformiat, phenyletylformiat and the like) represents an "arylalkyloxy" group as defined above attached through a carbonyl group.

The term "alkyloxycarbonylalkyl" represents an "alkyloxycarbonyl" group as defined above attached through an "alkyl" group as defined above having the indicated number of carbon atoms.

The term "arylalkyloxycarbonylalkyl" represents an "arylalkyloxycarbonyl" group as defined above attached through an "alkyl" group as defined above having the indicated number of carbon atoms.

The term "alkylthio" (e.g. methylthio, ethylthio, propylthio, cyclohexenylthio and the like) represents an "alkyl" group as defined above having the indicated number of carbon atoms attached through a sulfur bridge.

The term "arylalkylthio" (e.g. phenylmethylthio, phenylethylthio, and the like) represents an "arylalkyl"

group as defined above having the indicated number of carbon atoms attached through a sulfur bridge.

The term "alkylthioalkyl" represents an "alkylthio" group attached through an alkyl group as defined above having the indicated number of carbon atoms.

The term "arylalkylthioalkyl" represents an "arylalkylthio" group attached through an alkyl group as defined above having the indicated number of carbon atoms.

The term "alkylamino" (e.g. methylamino, diethylamino, butylamino, N-propyl-N-hexylamino, (2-cyclopentyl) propylamino, hexenylamino, pyrrolidinyl, piperidinyl and the like) represents one or two "alkyl" groups as defined above having the indicated number of carbon atoms attached through an amine bridge. The two alkyl groups may be taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1$–$C_6$alkyl, aryl, aryl$C_1$–$C_6$alkyl, hydroxy, $C_1$–$C_6$alkyloxy, $C_1$–$C_6$alkyloxy$C_1$–$C_6$alkyl, $NR_9R_{10}$, $C_1$–$C_6$alkylamino$C_1$–$C_6$alkyl substituent wherein the alkyl and aryl groups are optionally substituted as defined in the definition section and $R_9$ and $R_{10}$ are defined as above.

The term "arylalkylamino" (e.g. benzylamino, diphenylethylamino and the like) represents one or two "arylalkyl" groups as defined above having the indicated number of carbon atoms attached through an amine bridge. The two "arylalkyl" groups may be taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1$–$C_6$alkyl, aryl, aryl$C_1$–$C_6$alkyl, hydroxy, $C_1$–$C_6$alkyloxy, $C_1$–$C_6$alkyloxy$C_1$–$C_6$alkyl, $NR_9R_{10}$, $C_1$–$C_6$alkylamino$C_1$–$C_6$alkyl substituent wherein the alkyl and aryl groups are optionally substituted as defined in the definition section and $R_9$ and $R_{10}$ are defined as above.

The term "alkylaminoalkyl" represents an "alkylamino" group attached through an alkyl group as defined above having the indicated number of carbon atoms.

The term "arylalkylaminoalkyl" represents an "arylalkylamino" group attached through an alkyl group as defined above having the indicated number of carbon atoms.

The term "arylalkyl" (e.g. benzyl, phenylethyl) represents an "aryl" group as defined below attached through an alkyl having the indicated number of carbon atoms or substituted alkyl group as defined above. The term "alkylcarbonyl" (e.g. cyclooctylcarbonyl, pentylcarbonyl, 3-hexenylcarbonyl) represents an "alkyl" group as defined above having the indicated number of carbon atoms attached through a carbonyl group.

The term "arylalkylcarbonyl" (e.g. phenylcyclopropylcarbonyl, phenylethylcarbonyl and the like) represents an "arylalkyl" group as defined above having the indicated number of carbon atoms attached through a carbonyl group.

The term "alkylcarbonylalkyl" represents an "alkylcarbonyl" group attached through an "alkyl" group as defined above having the indicated number of carbon atoms.

The term "arylalkylcarbonylalkyl" represents an "arylalkylcarbonyl" group attached through an alkyl group as defined above having the indicated number of carbon atoms.

The term "alkylcarboxy" (e.g. heptylcarboxy, cyclopropylcarboxy, 3-pentenylcarboxy) represents an "alkylcarbonyl" group as defined above wherein the carbonyl is in turn attached through an oxygen bridge.

The term "arylalkylcarboxy" (e.g. benzylcarboxy, phenylcyclopropylcarboxy and the like) represents an "arylalkylcarbonyl" group as defined above wherein the carbonyl is in turn attached through an oxygen bridge.

The term "alkylcarboxyalkyl" represents an "alkylcarboxy" group attached through an "alkyl" group as defined above having the indicated number of carbon atoms.

The term "arylalkylcarboxyalkyl" represents an "arylalkylcarboxy" group attached through an "alkyl" group as defined above having the indicated number of carbon atoms.

The term "alkylcarbonylamino" (e.g. hexylcarbonylamino, cyclopentylcarbonyl-aminomethyl, methylcarbonylaminophenyl) represents an "alkylcarbonyl" group as defined above wherein the carbonyl is in turn attached through the nitrogen atom of an amino group. The nitrogen atom may itself be substituted with an alkyl or aryl group.

The term "arylalkylcarbonylamino" (e.g. benzylcarbonylamino and the like) represents an "arylalkylcarbonyl" group as defined above wherein the carbonyl is in turn attached through the nitrogen atom of an amino group. The nitrogen atom may itself be substituted with an alkyl or aryl group.

The term "alkylcarbonylaminoalkyl" represents an "alkylcarbonylamino" group attached through an "alkyl" group as defined above having the indicated number of carbon atoms. The nitrogen atom may itself be substituted with an alkyl or aryl group.

The term "arylalkylcarbonylaminoalkyl" represents an "arylalkylcarbonylamino" group attached through an "alkyl" group as defined above having the indicated number of carbon atoms. The nitrogen atom may itself be substituted with an alkyl or aryl group.

The term "alkylcarbonylaminoalkylcarbonyl" represents an alkylcarbonylaminoalkyl group attached through a carbonyl group. The nitrogen atom may be further substituted with an "alkyl" or "aryl" group.

The term "aryl" represents an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g., 3-indolyl, 4-imidazolyl). The aryl substituents are independently selected from the group consisting of halo, nitro, cyano, trihalomethyl, hydroxypyranyl, $C_1$–$C_6$alkyl, aryl, aryl$C_1$–$C_6$alkyl, hydroxy, $COOR_5$, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkyl-thio$C_1$–$C_6$alkyl, arylthio, aryl$C_1$–$C_6$alkylthio, aryl$C_1$–$C_6$alkylthio$C_1$–$C_6$alkyl, $NR_6R_7$, $C_1$–$C_6$alkylamino, $C_1$–$C_6$alkylamino$C_1$–$C_6$alkyl, arylamino, aryl$C_1$–$C_6$alkylamino, aryl$C_1$–$C_6$alkylamino$C_1$–$C_6$alkyl, di(aryl$C_1$–$C_6$alkyl)-amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkyl-carbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$alkyl, aryl$C_1$–$C_6$alkylcarboxy, aryl$C_1$–$C_6$alkyl-carboxy$C_1$–$C_6$alkyl, $C_1$–$C_6$alkylcarbonylamino, $C_1$–$C_6$alkylcarbonylamino$C_1$–$C_6$alkyl, -carbonyl$NR_6C_1$–$C_6$alkyl$COR_8$, aryl$C_1$–$C_6$alkyl-carbonylamino, aryl$C_1$–$C_6$alkylcarbonylamino$C_1$–$C_6$alkyl, —$CONR_6R_7$, or -$C_1$–$C_6$alkyl-$CONR_6R_7$;

wherein $R_5$, $R_6$, $R_7$ and $R_8$ are defined as above and the alkyl and aryl groups are optionally substituted as defined in the definition section;

The definition of aryl includes but is not limited to phenyl, biphenyl, indenyl, fluorenyl, naphthyl (1-naphthyl, 2-naphthyl), pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), isoxazolyl (3-isoxazolyl, 4-isoxazolyl, 5-isoxazolyl), thiazolyl (2-thiazolyl, 4-thiazolyl, 5-thiazolyl), 1,3,4-oxadiazol-2-yl, 1,3,4-thiadiazol-2-yl, tetrazol-5-yl, thiophenyl (2-thiophenyl, 3-thiophenyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]-thiophenyl (2-(2,3-dihydro-benzo[b]thiophenyl), 3-(2,3-dihydro-benzo[b]-thiophenyl), 4-(2,3-dihydro-benzo[b]thiophenyl), 5-(2,3-dihydro-benzo[b]-thiophenyl), 6-(2,3-dihydro-benzo[b]thiophenyl), 7-(2,3-dihydro-benzo[b]-thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]-azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), piperidinyl (2-piperidinyl, 3-piperidinyl, 4-piperidinyl), pyrrolidinyl (1-pyrrolidinyl, 2-pyrrolidinyl, 3-pyrrolidinyl), phenylpyridyl (2-phenylpyridyl, 3-phenylpyridyl, 4-phenylpyridyl), phenylpyrimidinyl (2-phenylpyrimidinyl, 4-phenylpyrimidinyl, 5-phenylpyrimidinyl, 6-phenylpyrimidinyl), phenylpyrazinyl, phenylpyridazinyl (3-phenyl-pyridazinyl, 4-phenylpyridazinyl, 5-phenyl-pyridazinyl).

The term "arylcarbonyl" (e.g. 2-thiophenylcarbonyl, 3-methoxyanthrylcarbonyl, oxazolylcarbonyl) represents an "aryl" group as defined above attached through a carbonyl group.

The term "arylalkylcarbonyl" (e.g. (2,3-dimethoxyphenyl)-propylcarbonyl, (2-chloronaphthyl)pentenylcarbonyl, imidazolylcyclo-pentylcarbonyl) represents an "arylalkyl" group as defined above wherein the "alkyl" group is in turn attached through a carbonyl.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds of formula 1 and formula 2, where a basic or acidic group is present in the structure, are also included within the scope of this invention. When an acidic substituent is present, such as —COOH or —P(O)(OH)$_2$, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, acetate, oxalate, maleate, fumarate, citrate, palmoate, methanesulfonate, p-toluenesulfonate, and the like, can be used as the dosage form.

Also, in the case of the —COOH or —P(O)(OH)$_2$ being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other.

DETAILED DESCRIPTION

A preferred embodiment of this application relates to compounds having the structures shown in Formula 3 and Formula 4:

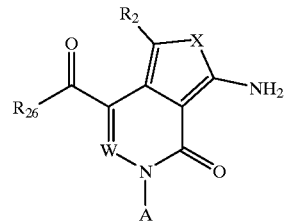

Formula 3

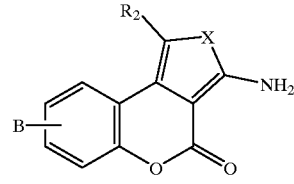

Formula 4 wherein
(i) $R_2$, X and W are defined as above,
(ii) $R_{26}$ is $OR_{21}$, $NR_{22}R_{23}$, wherein $R_{21}$, $R_{22}$ and $R_{23}$ are independently selected from hydrogen, hydroxy, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy, aryl$C_1$–$C_6$alkylcarboxy, $C_1$–$C_6$alkyloxycarbonyl$C_1$–$C_6$alkyl, aryl$C_1$–$C_6$alkyloxy-carbonyl$C_1$–$C_6$alkyl, $C_1$–$C_6$alkyloxycarbonylaryl$C_1$–$C_6$alkyl; wherein the alkyl and aryl groups are optionally substituted or $R_{22}$ and $R_{23}$ are independently a saturated or partial saturated cyclic 5,6 or 7 membered amine or lactam; wherein the alkyl and aryl groups are optionally substituted or $R_{22}$ and $R_{23}$ are taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1$–$C_6$alkyl, aryl, aryl$C_1$–$C_6$alkyl, hydroxy, $C_1$–$C_6$alkyloxy, $C_1$–$C_6$alkyloxy$C_1$–$C_6$alkyl, $NR_9R_{10}$ or $C_1$–$C_6$alkylamino$C_1$–$C_6$alkyl substituent; wherein $R_9$ and $R_{10}$ are defined as above and the alkyl and aryl groups are optionally substituted or $R_{22}$ and $R_{23}$ are independently -$C_1$–$C_6$alkylCONR$_6$R$_7$ wherein $R_6$ and $R_7$ are defined as above and the alkyl and aryl groups are optionally substituted or $R_{26}$ is selected from

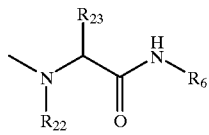

wherein $R_6$, $R_{22}$ and $R_{23}$ are defined as above;

(iii) A is selected from hydrogen, $C_1$–$C_6$alkyl, aryl, aryl$C_1$–$C_6$alkyl or from

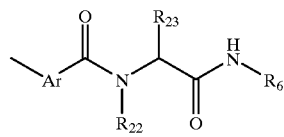

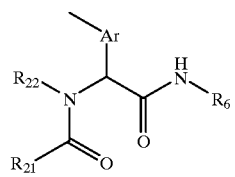

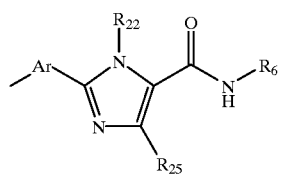

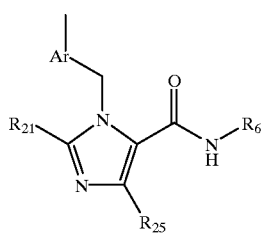

wherein Ar is aryl and $R_{21}$, $R_{22}$, $R_{23}$, and $R_{25}$ are independently selected from the group consisting of hydrogen, $C_1$–$C_6$alkyl, aryl, aryl$C_1$–$C_6$alkyl, wherein the alkyl and aryl groups are optionally substituted as defined above and (iv) B is selected from hydrogen, halo, nitro, cyano, COOH, $C_1$–$C_6$alkyl, aryl, aryl$C_1$–$C_6$alkyl, $C_1$–$C_6$alkyloxy, $C_1$–$C_6$alkyloxy$C_1$–$C_6$alkyl, $C_1$–$C_6$alkylthio, $C_1$–$C_6$alkylthio$C_1$–$C_6$alkyl, COR$_8$, $C_1$–$C_6$alkylamino, $C_1$–$C_6$alkylamino$C_1$–$C_6$alkyl, —CONR$_6$R$_7$$C_1$–$C_6$alkylcarbonyl, $C_1$–$C_6$alkylcarbonyl$C_1$–$C_6$alkyl, $C_1$–$C_6$alkylcarbonylamino, $C_1$–$C_6$alkylcarbonylamino$C_1$–$C_6$alkyl, arylcarbonyl, aryl$C_1$–$C_6$alkylcarbonyl, or B is selected from

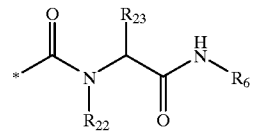

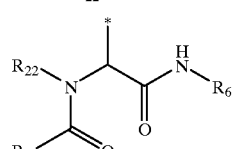

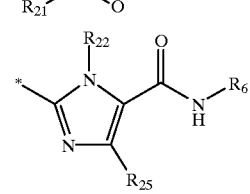

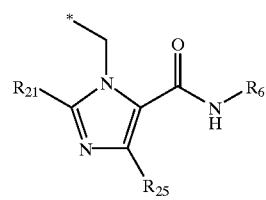

wherein $R_6$, $R_{21}$, $R_{22}$, $R_{23}$, and $R_{25}$ are defined as above and (*) indicates the point of attachment of B.

The following compounds are preferred:

7-Amino-4-ethylsulfanyl-2-(4-methoxy-phenyl)thieno[3,4-d]pyridazin-1(2H)-one;
3-Amino-4H-naphtho[2,1-b]thieno[3,4-d]pyran-4-one;
3-Amino-8-methoxy-4H-thieno[3,4-c]chromen-4-one;
3-Amino-7-fluoro-4H-thieno[3,4-c]chromen-4-one;
5-Amino-3-(4-carboxy-phenyl)-4-oxo-3,4-dihydro-thieno[3,4-d]pyridazine-1-carboxylic acid ethyl ester;
3-Amino-7-methoxy-4H-thieno[3,4-c]chromen-4-one;
3-Amino-4H-thieno[3,4-c]chromen-4-one;
7-Amino-4-ethylsulfanyl-2-phenyl-thieno[3,4-d]pyridazin-1 (2H)-one;
5-Amino-3-(3-carboxy-phenyl)-4-oxo-3,4-dihydro-thieno[3,4-d]pyridazine-1-carboxylic acid ethyl ester;
5-Amino-7-bromo-4-oxo-3-phenyl-3,4-dihydro-thieno[3,4-d]pyridazine-1-carboxylic acid ethyl ester;
3-Amino-7-morpholin-4-yl-4H-thieno[3,4-c]chromen-4-one;
5-Amino-4-oxo-3-phenyl-3,4-dihydro-thieno[3,4-d]pyridazine-1-carbothioic acid amide;
7-Amino-4-cyano-2-(2-methoxy-phenyl)-1-oxo-1,2-dihydro-thieno[3,4-d]pyridazine-5-carboxylic acid ethyl ester;
3-Amino-9-methoxy-4H-thieno[3,4-c]chromen-4-one;
3-Amino-4H-naphtho[2,1-b]thieno[3,4-d]pyran-4-one;
3-Amino-1-bromo-4H-thieno[3,4-c]chromen-4-one;
5-Amino-4-oxo-3-phenyl-3,4-dihydro-thieno[3,4-d]pyridazine-1-carbonitrile;
5-Amino-4-oxo-3-phenyl-3,4-dihydro-thieno[3,4-d]pyridazine-1-carboxylicacid hydrazide;

5-Amino-4-oxo-3-phenyl-3,4-dihydro-thieno[3,4-d]
pyridazine-1-carboxylic acid ethyl ester;
5-Amino-4-oxo-3-phenyl-3,4-dihydro-thieno[3,4-d]
pyridazine-1-carboxylic acid;
5-Amino-3-(3-methoxy-phenyl)-4-oxo-3,4-dihydro-thieno
[3,4-d]pyridazine-1-carboxylic acid ethyl ester;
3-Amino-8-bromo-4H-thieno[3,4-c]chromen-4-one;
3-Amino-8-chloro-4H-thieno[3,4-c]chromen-4-one;
3-Amino-4H-thieno[3,4-c]chromen-4-one-8-carboxylic
acid ethyl ester;
5-Amino-3-(4-((1-benzylcarbamoyl-pentyl)isopropyl-
carbamoyl)phenyl)-4-oxo-3,4-dihydro-thieno[3,4-d]
pyridazine-1-carboxylic acid ethyl ester;
5-Amino-3-(4-((1-benzylcarbamoyl-pentylcarbamoyl)
phenyl)-4-oxo-3,4-dihydro-thieno[3,4-d]pyridazine-1-
carboxylic acid ethyl ester;
5-Amino-3-(4-((1-(5-carboxy-pentylcarbamoyl)-pentyl)
isopropyl-carbamoyl)phenyl)-4-oxo-3,4-dihydro-thieno
[3,4-d]pyridazine-1-carboxylic acid ethyl ester;
5-Amino-3-(4-chloro-phenyl)-4-oxo-3,4-dihydro-thieno[3,
4-d]pyridazine-1-carboxylic acid ethyl ester;
5-Amino-7-bromo-4-oxo-3-phenyl-3,4-dihydro-thieno[3,4-
d]pyridazine-1-carboxylic acid ethyl ester;
5-Amino-3-(4-iodo-phenyl)-4-oxo-3,4-dihydro-thieno[3,4-
d]pyridazine-1-carboxylic acid ethyl ester;
5-Amino-3-(3-iodo-phenyl)4-oxo-3,4-dihydro-thieno[3,4-
d]pyridazine-1-carboxylic acid ethyl ester;
5-Amino-3-(4-benzyloxycarbonyl-phenyl)-4-oxo-3,4-
dihydro-thieno[3,4-d]pyridazine-1-carboxylic acid ethyl
ester; 5-Amino-3-(3-methoxy-phenyl)-4-oxo-3,4-
dihydro-thieno[3,4-d]pyridazine-1-carboxylic acid;
7-Amino-4-ethanesulfinyl-2-phenyl-2H-thieno[3,4-d]
pyridazin-1-one;
7-Amino-4-ethanesulfonyl-2-phenyl-2H-thieno[3,4-d]
pyridazin-1-one;
(7-Amino-4-methyl-1-oxo-1H-thieno[3,4-d]pyridazin-2-yl)
acetic acid ethyl ester;
7-Amino-4-(5-oxo-4,5-dihydro[1,3,4]oxadiazol-2-yl)-2-
phenyl-2H-thieno[3,4-d]pyridazin-1-one;
[5-Amino-3-(4-methoxy-phenyl)-4-oxo-3,4-dihydro-thieno
[3,4-d]pyridazin-1-yl]carbamic acid tert-butyl ester; and
4,7-Diamino-2-(4-methoxy-phenyl)-2H-thieno[3,4-d]
pyridazin-1-one;
or a pharmaceutically acceptable salt thereof.

These compounds were evaluated for biological activity with a truncated form of PTP1B (corresponding to the first 321 amino acids), which was expressed in *E. coli* and purified to apparent homogeneity using published procedures well-known to those skilled in the art. The enzyme reactions were carried out using standard conditions essentially as described by Burke et al. (*Biochemistry* 35; 15989–15996 (1996)). The assay conditions were as follows. Appropriate concentrations of the compounds of the invention were added to the reaction mixtures containing different concentrations of the substrate, p-nitrophenyl phosphate (range: 0.16 to 10 mM—final assay concentration). The buffer used was 100 mM sodium acetate pH 5.5, 50 mM sodium chloride, 0.1% (w/v) bovine serum albumin and 5 mM dithiothreitol (total volume 100 ml). The reaction was started by addition of the enzyme and carried out in microliter plates at 25° C. for 60 minutes. The reactions were stopped by addition of NaOH. The enzyme activity was determined by measurement of the absorbance at 405 nm with appropriate corrections for absorbance at 405 nm of the compounds and p-nitrophenyl phosphate. The data were analyzed using nonlinear regression fit to classical Michaelis Menten enzyme kinetic models. Inhibition is expressed as $K_i$ values in $\mu$M. The results of representative experiments are shown in Table 1

TABLE 1

Inhibition of classical PTP1B by compounds of the invention

| Example no. | PTP1B $K_i$ values ($\mu$M) |
|---|---|
| 2 | 2 |
| 3 | 4 |

THE SYNTHESIS OF THE COMPOUNDS

In accordance with one aspect of the invention, the compounds of the invention are prepared as illustrated in the following reaction scheme:

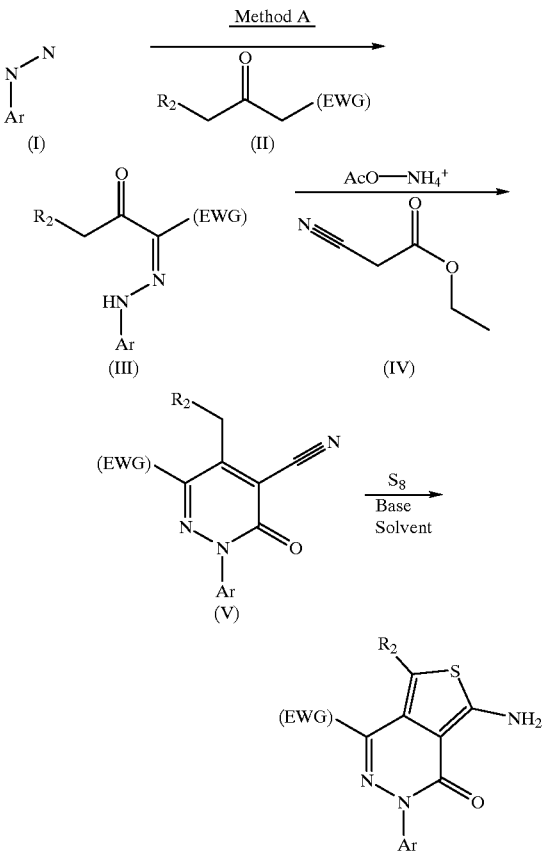

By allowing a diazonium salt (I) to react with a ketone (II), and subsequently cyclising the intermediate (III) with ethyl cyanoacetate (IV), and by allowing the intermediate (V) to react with sulfur wherein Ar and $R_2$ are defined as above and EWG is CN, $COOR_5$, $CONR_5R_7$, $COR_8$ wherein $R_5$, $R_6$, $R_7$ and $R_8$ are defined as above.

Method B

By allowing a hydrazone of formula (VI) prepared as above in Method A to react with tert-butyl hypochloride followed by deacetylation with methanol, and by allowing intermediate (VII) to react with a nucleophile (IX), and subsequently cyclising the intermediate (X) with ethyl cyanoacetate (IV) followed by cyclisation by allowing the intermediate to react with sulfur wherein Ar, $R_2$ are defined as above and X is sulfur and $R_5$ is $C_1$–$C_6$alkyl, aryl, aryl$C_1$–$C_6$alkyl wherein the alkyl and aryl groups are optionally substituted as defined above.

Method C

By allowing an aryl ketone (XI) to react with ethyl cyanoacetate (IV), and by subsequently cyclising the intermediate (XII) with sulfur wherein Z, $R_2$ and B are defined as above.

Method D

By allowing a carboxylic acid (XIII), a primary amine (XIV) and an aldehyde (XV) to react with a isocyanide (XVI) wherein $R_6$, $R_{26}$, $R_{27}$, and $R_{28}$ are independently selected from the group consisting of hydrogen, $C_1$–$C_6$alkyl, aryl, aryl$C_1$–$C_6$alkyl as defined above and the alkyl and aryl groups are optionally substituted defined as above.

In a preferred method, the above described four component Ugi reaction can be carried out by attaching any one of the components to a solid support. Hence, the synthesis can be accomplished in a combinatorial chemistry fashion.

Method E

By allowing a carboxylic acid (XIII), a primary amine (XIV) and a ketoaldehyde (XVII) to react with a isocyanide (XVI) and by subsequently cyclising the intermediate (XVIII) with ammonium acetate wherein $R_6$, $R_{26}$, $R_{27}$, and $R_{28}$ defined as above.

In a preferred method, the above described four component Ugi reaction can be carried out by attaching any one of the components to a solid support. Hence, the synthesis can be accomplished in a combinatorial chemistry fashion.

The present invention also has the objective of providing suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavoring agents, coloring agents and preserving agents in order to produce pharmaceutically elegant and palatable preparations. The tablets contain the acting ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such expicients may be (1) suspending agent such as sodium carboxymethyl cellulose, methyl cellulose, hydroxypropylmethyl-cellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylen-oxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The Compounds of the invention may also be administered in the form of suppositories for rectal administration. These compositions can be prepared by mixing the drug with a suitable non-rritating excipient which is solid at ordinary temperature but liquid at the rectal temperature and will therefore melt in the rectum to release the drug. Such materials are cocoa butter and polyethylene glycols.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidyl-cholines.

For topical use, creams, ointments, jellies, solutions or suspensions, etc., containing the compounds of Formula 1 are employed.

Dosage levels of the compounds of the present invention are of the order of about 0.5 mg to about 100 mg per kilogram body weight, with a preferred dosage range between about 20 mg to about 50 mg per kilogram body weight per day (from about 25 mg to about 5 g's per patient per day). The amount of active ingredient that may be combined with the carrier materials to produce a single dosage will vary depending upon the host treated and the particular mode of administration. For example, a formulation intended for oral administration to humans may contain 5 mg to 1 g of an active compound with an appropriate and convenient amount of carrier material which may vary from about 5 to about 95 percent of the total composition. Dosage unit forms will generally contain between from about 5 mg to about 500 mg of active ingredient.

It will be understood, however, that the specific dose level for any particular patient will depend upon a variety of factors including the activity of the specific compound employed, the age, body weight, general health, gender, diet, time of administration, route of administration, rate of excretion, drug combination and the severity of the particular disease undergoing therapy. The dosage needs to be individualized by the clinician.

EXAMPLES

The process for preparing compounds of Formula 1, Formula 2 Formula 3 and Formula 4 and preparations containing them is further illustrated in the following examples, which, however, are not to be construed as limiting.

Hereinafter, TLC is thin layer chromatography, $CDCl_3$ is deuterio chloroform and DMSO-$d_6$ is hexadeuterio dimethylsulfoxide. The structures of the compounds are confirmed by either elemental analysis or NMR, where peaks assigned to characteristic protons in the title compounds are presented where appropriate. $^1H$ NMR shifts ($\delta_H$) are given in parts per million (ppm) downfield from tetramethylsilane (TMS) as internal reference standard. M.p.: is melting point and is given in °C. and is not corrected. Column chromatography/silica gel purification was carried out using the technique described by W. C. Still et al., *J. Org. Chem.* 43: 2923 (1978) on Merck silica gel 60 (Art. 9385). HPLC analyses were performed using 5 µm C 18 4×250 mm column eluted with various mixtures of water and acetonitrile, flow=1 ml/min, as described in the experimental section.

Compounds used as starting material are either known compounds or compounds which can readily be prepared by methods known per se.

Example 1

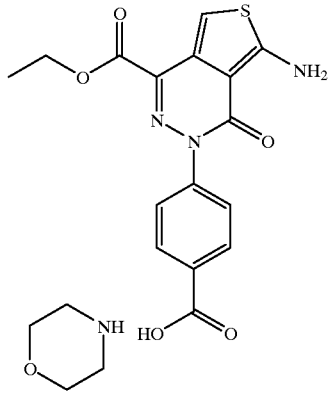

5-Amino-3-(4-carboxy-phenyl)-4-oxo-3,4-dihydro-thieno[3,4-d]pyridazine-1-carboxylic acid ethyl ester, morpholinium salt 4-Amino-benzoic acid (40 g, 0.28 mol) was dissolved in a mixture of concentrated hydrochloric acid (84 ml) and water (84 ml). To the resulting mixture was added dropwise at 5° C. a solution of sodium nitrite (21.5 g, 0.31 mol) in water (100 ml). The resulting diazonium salt was added to a mixture of sodium acetate (116 g, 0.85 mol), ethanol (300 ml) and ethyl acetoacetate (36.5 ml, 0.28 mol) at room temperature. The resulting mixture was diluted with a 50% aqueous ethanol (1 l) and stirred for 1 h at room temperature. The precipitate was filtered off and washed with water (1 l), 50% aqueous ethanol (1 l) and heptane (2×300 ml) and dried in vacuo at 50 ° C. for 48 h affording 77 g (98%) of 4-[N'-(1-ethoxycarbonyl-2-oxo-propylidene)-hydrazino]-benzoic acid as a solid.

A mixture of the above hydrazon (40 g, 0.14 mol), ethyl cyanoacetate (37 ml) and ammonium acetate (22.2 g, 0.29 mol) was heated at reflux (105° C.) for 3 h. 50% aqueous ethanol (100 ml) was added at 60° C. and the resulting mixture was cooled to 10° C. The precipitate was filtered off and washed with 50% aqueous ethanol (4×50 ml) and heptane (3×50 ml) and dried in vacuo at 50° C. for 18 h affording 17.8 g (38%). The aqueous phase was acidified to pH=2.5 with concentrated hydrochloric acid and the precipitate was filtered off and washed with 50% aqueous ethanol (2×100 ml) and heptane (1×100 ml) and dried in vacuo at 50° C. for 18 h affording 13.8 g (29%).

A total of 31.6 g (67%) of 1-(4-carboxy-phenyl)-5-cyano-4-methyl-6-oxo-1,6-dihydro-pyridazine-3-carboxylic acid ethyl ester as a solid was isolated.

To a mixture of the above pyridazine (17.00 g, 51.94 mmol) in ethanol (45 ml) was added sulfur (1.75 g, 54.53 mmol) and morpholin (10.2 ml). The resulting mixture was heated at 60° C. for 3 h. The cooled reaction mixture was left over night and diluted with ethanol (10 ml). The precipitate was filtered off and washed with a mixture of ethanol and diethyl ether (1:1) (3×60 ml) and with diethyl ether (3×50 ml), dried in vacuo at 50° C. for 6 h afforded 22.11 g (95%) of the title compound as a solid.

Calculated for $C_{20}H_{22}N_4O_6S_1$; C, 53.80%; H, 4.97%; N, 12.55%. Found: C, 54.05%; H, 5.35%; N, 12.32%.

Example 2

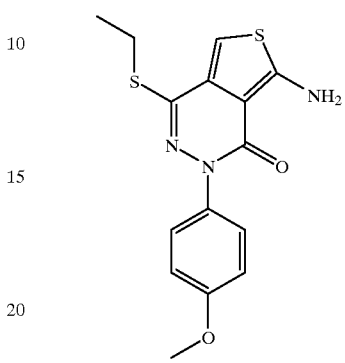

7-Amino-4-ethylsulfanyl-2-(4-methoxy-phenyl)thieno[3,4-d]pyridazin-1(2H)-one

4-Amino-anisole (15 g, 0.12 mol) was dissolved in a mixture of concentrated hydrochloric acid (36 ml) and water (36 ml). To the resulting mixture was added dropwise at 5° C. a solution of sodium nitrite (9.2 g, 0.13 mol) in water (45 ml). The resulting diazonium salt was added to a mixture of sodium acetate (30 g, 0.37 mol), ethanol (125 ml) and pentane-2,4-dione (12.2 g, 0.12 mol) at room temperature. The resulting mixture was stirred for 1 h at room temperature. The precipitate was filtered off and washed with water (2×150 ml), ethanol (2×50 ml) and dried in vacuo at 50° C. for 18 h affording 17 g (60%) of 3-[(4-methoxy-phenyl)-hydrazono]-pentane-2,4-dione as a solid.

To a solution of the above hydrazon (15 g, 0.064 mol) in chloroform (50 ml) cooled in a ice bath was added dropwise t-butylhypochlorit (7.6 g, 0.070 mol). The resulting mixture was stirred at room temperature for 1 h. The volatiles were evaporated in vacuo affording crude (17.2 g) of 3-chloro-3-[(4-methoxy-phenyl)hydrazono]pentane-2,4-dione as an oil. The crude oil (17.2 g) was dissolved in methanol (100 ml) and heated at reflux temperature for 5 min. The volatiles were evaporated in vacuo affording crude 11.6 g (80%) of pyruvoyl chloride 1-(4-methoxyphenylhydrazone) as a solid.

To a mixture of sodium ethoxide (50 ml; prepared from 0.51 g sodium and 50 ml ethanol) and ethyl mercaptane (1.7 ml, 23 mmol) was added in small portion the above pyruvoyl chloride (5 g, 22 mmol). The resulting mixture was stirred at room temperature for 18 h and diluted with water (100 ml) and extracted with diethyl ether (2×75 ml). The combined organic extracts were washed with water (2×50 ml), saturated aqueous sodium chloride (50 ml), dried (MgSO$_4$), filtered and evaporated in vacuo affording 5.1 g (92%) of 1-ethylsulfanyl-1,2-propanedione-1-(4-methoxyphenylhydrazone) as a solid.

A mixture of the above ethylsulfanyl (5.1 g, 20.2 mmol), ethyl cyanoacetate (2.4 g, 21.2 mmol) and ammonium acetate (3.1 g, 40.4 mmol) was heated at reflux (105° C.) for 1.5 h. 75% aqueous ethanol (75 ml) was added at 60° C. and the resulting mixture was cooled to 10° C. The precipitate was filtered off and washed with 50% aqueous ethanol (4×50 ml) and dried in vacuo at 50° C. for 18 h affording 4.2 g (69%) of 6-ethylsulfanyl-2-(4-methoxy-phenyl)-5-methyl-3-oxo-2,3-dihydro-pyridazine-4-carbonitrile as a solid.

To a mixture of the above pyridazine (4.0 g, 13.8 mmol) in ethanol (20 ml) was added sulfur (442 mg, 13.8 mmol) and morpholin (2 ml). The resulting mixture was heated at reflux temperature for 2 h. The reaction mixture was cooled and the precipitate was filtered off and washed with water (2× 20 ml) and diethyl ether (2×25 ml), dried in vacuo at 50° C. for 18 h which afforded 2.2 g (50%) of the title compound as a solid.

Calculated for $C_{15}H_{15}N_3O_2S_2$; C, 53.31%; H, 4.62%; N, 12.43%. Found: C, 53.47%; H, 4.28%; N, 12.03%.

Example 3

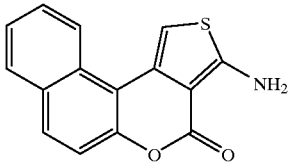

3-Amino4H-naphtho[2,1-b]thieno[3,4-d]pyran-4-one

To a mixture of sodium ethoxide (100 ml; prepared from 1.38 g sodium and 100 ml ethanol) and 2-hydroxy-1-acetonaphthone (11.29 g, 0.06 mol) was added ethyl cyanoacetate (11.1 ml, 0.1 mol). The resulting mixture was stirred at reflux temperature for 2 h. The reaction mixture was cooled in a ice bath and the precipitate was filtered off and washed with water (20 ml) and cold ethanol (3×20 ml), dried in vacuo at 50° C. for 18 h which afforded (9 g) of crude product. The crude product (9 g) was recrystallised from a mixture of acetone (1 l) and water (25 ml) affording 5.33 g (38%) of 1-methyl-3-oxo-3H-benzo[f]chromene-2-carbonitrile as a solid.

In a screw cap ampoule was added to a mixture of the above benzo[f]chromene (2.35 g, 10 mmol) in ethanol (20 ml), sulfur (321 mg, 10 mmol) and morpholin (1.3 ml). The resulting mixture was heated at 80° C. for 18 h. The reaction mixture was cooled and the precipitate was filtered off and washed with ethanol (2×20 ml) and carbon disulfide (2×20 ml), dried in vacuo at 50° C. for 18 h which afforded 1.82 g (68%) of the title compound as a solid.

M.p.: 221–222° C.

$^1$H NMR (300 MHz, DMSO-$d_6$) $\delta_H$ 7.36 (s, 1H, thiophen); 7.43 (d, 1H); 7.57 (t, 1H); 7.71 (t, 1H); 7.89–8.03 (m, 4H, $NH_2$ and 2 aromatic protons); 8.71 (d, 1H).

Calculated for $C_{15}H_9NO_2S$, 0.5 $H_2O$; C, 65.20%; H, 3.65%; N, 5.07%. Found: C, 65.27%; H, 3.32%; N, 5.19%.

The following compounds were prepared in a similar way as described in example 3.

Example 4

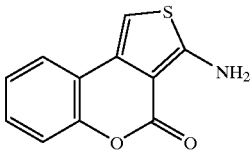

3-Amino-4H-thieno[3,4-c]chromen-4-one

Calculated for $C_{11}H_7NO_2S$; C, 60.82%; H, 3.25%; N, 6.45%. Found: C, 61.22%; H, 3.24%; N, 6.38%.

Example 5

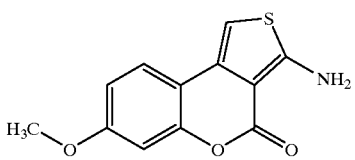

3-Amino-7-methoxy-4H-thieno[3,4-c]chromen-4-one

Calculated for $C_{12}H_9NO_3S$; C, 58.29%; H, 3.67%; N, 5.66%. Found: C, 58.10%; H, 3.7%; N, 5.8%.

Example 6

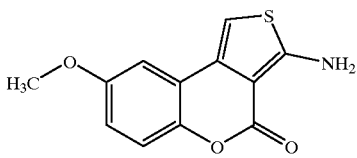

3-Amino-8-methoxy-4H-thieno[3,4-c]chromen-4-one

Calculated for $C_{12}H_9NO_3S$; C, 58.29%; H, 3.67%; N, 5.66%. Found: C, 58.39%; H, 3.73%; N, 5.70%.

Example 7

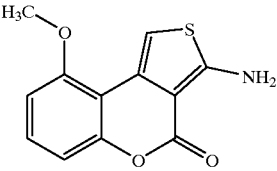

3-Amino-9-methoxy-4H-thieno[3,4-c]chromen-4-one $^1$H NMR (300 MHz, DMSO-$d_6$) $\delta_H$ 3.95 (s, 3H), 6.83 (d, 1H), 6.90 (d, 1H), 6.95 (s, 1H, thiophen); 7.30 (t, 1H); 7.75 (bs, 2H, $NH_2$).

Example 8

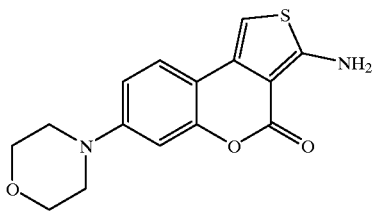

3-Amino-7-morpholin-4-yl-4H-thieno[3,4-c]chromen-4-one $^1$H NMR (300 MHz, DMSO-d$_6$) δ$_H$ 3.18 (m, 4H), 3.73 (m, 4H), 6.61 (s, 1H, thiophen); 6.70 (d, 1H); 6.85 (dd, 1H); 7.58–7.76 (m, 3H, NH$_2$ and one aromat).

Example 9

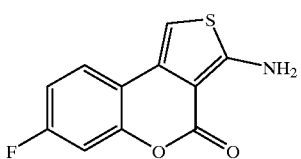

3-Amino-7-fluoro-4H-thieno[3,4-c]chromen4-one $^1$H NMR (300 MHz, DMSO-d$_6$) δ$_H$ 6.86 (s, 1H, thiophen); 7.05–7.21 (m, 2H); 7.81 (bs, 2H, NH$_2$); 7.92 (dd, 1H).

Example 10

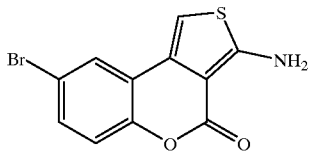

3-Amino-8-bromo-4H-thieno[3,4-c]chromen-4-one

Calculated for C$_{11}$H$_6$NBrO$_2$S; C, 44.61%; H, 2.04%; N, 4.73%. Found: C,44.60%; H, 1.97%; N, 4.62%.

Example 11

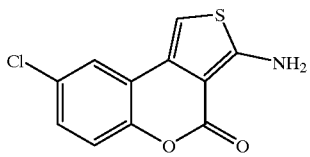

3-Amino-8-chloro-4H-thieno[3,4-c]chromen-4-one

Calculated for C$_{11}$H$_6$NClO$_2$S; C, 52.49%; H, 2.40%; N, 5.57%. Found: C, 52.72%; H, 2.40%; N, 5.50%.

Example 12

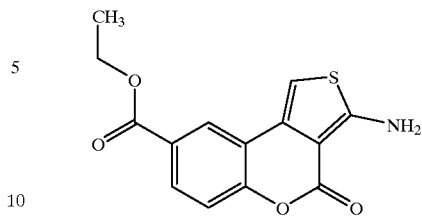

3-Amino-4H-thieno[3,4-c]chromen-4-one-8-carboxylic acid ethyl ester

Calculated for C$_{14}$H$_{11}$NO$_4$S; C, 58.12%; H, 3.83%; N, 4.84%. Found: C, 58.09%; H, 3.85%; N, 4.81%.

Example 13

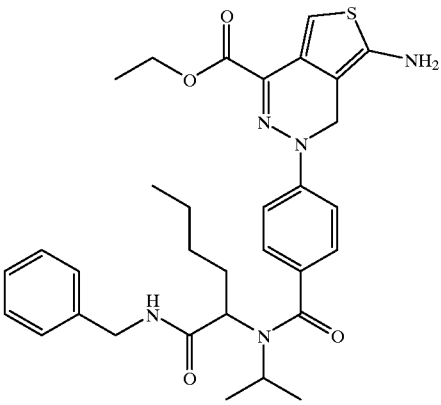

5-Amino-3-(4-((1-benzylcarbamoyl-pentyl)isopropyl-carbamoyl)phenyl)-4-oxo-3,4-dihydro-thieno[3,4-d]pyridazine-1-carboxylic acid ethyl ester To a solution of 5-amino-3-(4-carboxy-phenyl)-4-oxo-3,4-dihydro-thieno[3,4-d]pyridazine-1-carboxylic acid ethyl ester (9.0 mg, 0.025 mmol) in a mixture of methanol and tetrahydrofuran (200 ml, 1:1) was added isopropyl amine (25 μl, 0.025 mmol, 1.0 M in tetrahydrofuran), valeraldehyde (25 μl, 0.025 mmol, 1.0 M in tetrahydrofuran) and benzyl isocyanide (25 μl, 0.025 mmol, 1.0 M in tetrahydrofuran). The mixture was stirred at 45° C. for 64 h. After dilution with dichloromethane (1 ml), the mixture was purified on a preparative TLC plate using a mixture of methanol/ethyl acetate/hexane (1:4:4) as eluent. Spot eluting with R$_f$=0.66 was collected which afforded 6.3 mg (42%) of the title compound.

Example 14

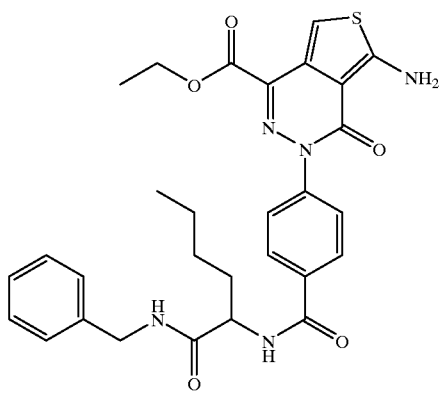

5-Amino-3-(4-((1-benzylcarbamoyl-pentylcarbamoyl)phenyl)-4-oxo-3,4-dihydro-thieno[3,4-d]pyridazine-1-carboxylic acid ethyl ester To 100 mg Rink resin (0.22 mmol/g, 0.022 mmol) was added 5-amino-3-(4-carboxy-phenyl)4-oxo-3,4-dihydro-thieno[3,4-d]pyridazine-1-carboxylic acid ethyl ester (1 ml, 0.01 mmol, 0.1 M in methanol/tetrahydrofuran (⅓)), valeraldehyde (200 ml, 0.2 mmol, 1.0 M in tetrahydrofuran) and benzyl isocyanide (200 ml, 0.2 mmol, 1.0 M in methanol). The mixture was stirred at 45° C. for 72 h followed by filtration and washing with tetrahydrofuran (5×100 ml), triethylamine (3×50 ml), tetrahydrofuran (5×50 ml), methanol (5×50 ml) and dichloromethane (5×50 ml). The resin was dried and then treated with 20% TFA in dichloromethane for 30 min. After filtration and washing with dichloromethane (5×50 ml), the filtrate was concentrated in vacuo and directly loaded onto a preparative TLC plate using a mixture of methanol/ethyl acetate/hexane (1:4:4) as eluent. Spot eluting with $R_f$=0.70 was collected which afforded 4.4 mg (36%) of the title compound as a solid.

$^1$H NMR (400 MHz, CD$_3$OD): $\delta_8$H 0.88 (t, 3H, J =6.4 Hz), 1.25–1.36 (m, 7H), 1.79 (m, 1H), 1.87 (m, 1H), 4.33–4.39 (m, 4H), 4.50–4.55 (m, 1 H), 7.13 (s, 1H), 7.20 (m, 1H), 7.26 (m, 4H), 7.69 (d, 2H, J 8.8 Hz), 7.92 (d, 2H, J =8.8 Hz).

MS (ES$^+$); Calculated 561.20; Found 562.03.

Example 15

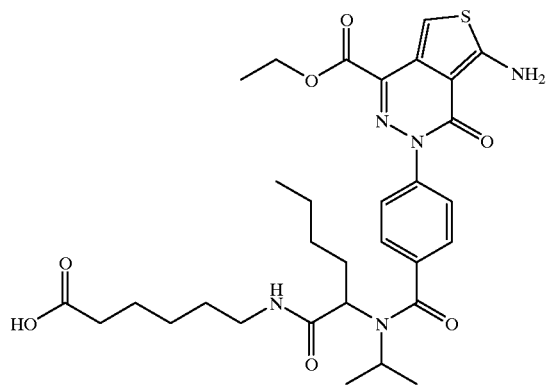

5-Amino-3-(4-((1-(5-carboxy-pentylcarbamoyl)-pentyl)isopropyl-carbamoyl)phenyl)-4-oxo-3,4-dihydro-thieno[3,4-d]pyridazine-1-carboxylic acid ethyl ester 6-Aminocaproic acid (100 g, 0.76 mol) was suspended in a mixture of ethylformate and N,N-dimethylformamide (1 l, 1:1) and heated at 100° C. for 18 h. The volatiles were evaporated in vacuo and the residue treated with ethyl acetate. The solid matter was filtered off and washed with ethyl acetate and air dried which afforded 115 g (95%) of 6-formyl hexanoic acid.

Diisopropylcarbondiimide (60 g, 0.48 mol) was added to a mixture of 6-formyl hexanoic acid (80 g, 0.5 mol), 4-N,N-dimethylaminopyridin (4 g, 33 mmol) and Wang-resin (140 g, 1.12 mmol/g) in dry tetrahydrofuran (1 l) under an atmosphere of nitrogen. The reaction mixture was sonicated for 6 h and then stirred at room temperature for 18 h. The resin was filtered off and washed with dichloromethane, methanol (repeatedly) and then dried in a vacuum desiccator for 18 h.

To a stirred mixture of the above 6-formyl hexanoic acid Wang-resin ester (165 g, 0.16 mol) in dichloromethane (3.2 l) was added triethylamine (222 ml, 1.6 mol), tetrachloromethane (155 ml, 1.6 mol) and triphenylphosphine (168 g, 0.64 mol). The resulting mixture was stirred at room temperature for 16 h under an atmosphere of nitrogen. The resin was filtered off and washed with N,N-dimethylformamide, dichloromethane, methanol, dichloromethane and dried in a vacuum desiccator for 18 h which afforded 6-isocyano-hexanoic acid Wang-resin ester.

To 24 mg of the above isocyanide resin (0.84 mmol/g, 0.02 mmol) was added 5-amino-3-(4-carboxy-phenyl)4-oxo-3,4-dihydro-thieno[3,4-d]pyridazine-1-carboxylic acid ethyl ester (1,0 ml, 0.01 mmol, 0.1 M in methanolltetrahydrofuran (1:3)), valeraldehyde (200 ml, 0.2 mmol, 1.0 M in tetrahydrofuran) and isopropyl amine (200 ml, 0.2 mmol, 1.0 M in tetrahydrofuran). The mixture was stirred at 45° C. for 72 h followed by filtration and washing with tetrahydrofuran (5×50 ml), triethylamine (3×50 ml), tetrahydrofuran (5×50 ml), methanol (5×50 ml) and dichloromethane (5×50 ml). The resin was dried and then treated with 20% TFA in dichloromethane for 30 min. After filtration and washing with dichloromethane (5×50 ml), the filtrate was concentrated in vacuo and the residue loaded onto a preparative TLC using a mixture of methanol/ethyl acetate/hexane (1:4:4) as eluent. Spot eluting with $R_f$=0.57 was collected which afforded 6.0 mg (48%) of the title compound as a solid.

MS (ES$^+$); Calculated 627.27; Found 628.07

The following compounds were prepared in a similar way as described in example 1.

Example 16

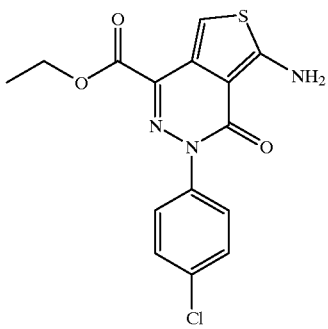

5-Amino-3-(4-chloro-phenyl)-4-oxo-3,4-dihydro-thieno[3,4-d]pyridazine-1-carboxylic acid ethyl ester M.p.: 187–189° C.;

Calculated for $C_{15}H_{12}N_3O_3S$; C, 51.51%; H, 3.46%; N, 12.01%. Found: C, 51.78%; H, 3.43%; N, 12.09%.

Example 17

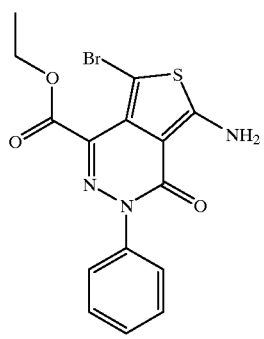

5-Amino-7-bromo-4-oxo-3-phenyl-3,4-dihydro-thieno[3,4-d]pyridazine-1-carboxylic acid ethyl ester M.p.: 112–114° C.;

Calculated for $C_{15}H_{12}BrN_3O_3S$; C, 45.70%; H, 3.07%; N, 10.66%. Found: C, 45.91%; H, 3.07%; N, 10.41%.

Example 18

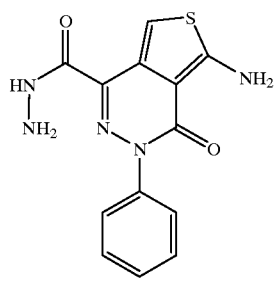

5-Amino-4-oxo-3-phenyl-3,4-dihydro-thieno[3,4-d]pyridazine-1-carboxylic acid hydrazide To a solution of 5-Amino-4-oxo-3-phenyl-3,4-dihydro-thieno[3,4-d]pyridazine-1-carboxylic acid ethyl ester (20 g, 0.063 mol, prepared as described in example 25) in ethanol (400 ml) was added hydrazine hydrate (3.3 g, 0.066 mol). The reaction mixture was stirred at reflux temperature for 6 h at which time an additional portion of hydrazine hydrate (3.3 g, 0.066 mol) was added and the resulting mixture was stirred for an additional 66 h at reflux temperature. An additional portion of hydrazine hydrate (1.5 g, 0.03 mol) was added and the reaction mixture was stirred for an additional 16 h at reflux temperature. The reaction mixture was cooled and the precipitated was filtered off, washed with small portions of ethanol and dried in vacuo at 50° C. for 18 h which afforded 17.9 g (94%) of the title compound as a solid.

$^1$H NMR (300 MHz, DMSO-$d_6$) $\delta_H$ 4.51 (bs, 2H, H$_2$NNHCO), 7.09 (s, 1 H, thiophen), 7.31 (t, 1 H), 7.43 (t, 2H), 7.57 (bs, 2H, NH$_2$), 7.65 (d, 1H), 9.58 (s, 1 H, H$_2$N-NHCO).

Example 19

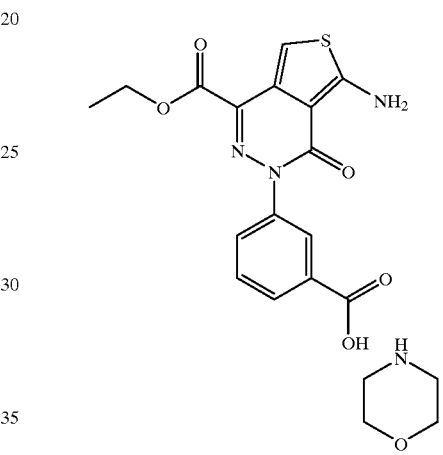

5-Amino-3-(3-carboxy-phenyl)-4-oxo-3,4-dihydro-thieno[3,4-d]pyridazine-1-carboxylic acid ethyl ester, morpholinium salt Calculated for $C_{20}H_{22}N_4O_6S$; C, 53.80%; H, 4.97%; N, 12.55%. Found: C, 53.74%; H, 5.23%; N, 12.40%.

Example 20

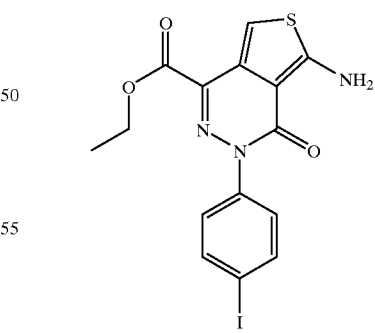

5-Amino-3-(4-iodo-phenyl)-4-oxo-3,4-dihydro-thieno[3,4-d]pyridazine-1-carboxylic acid ethyl ester M.p.: 198–200° C.;

Calculated for $C_{15}H_{12}IN_3O_3S$, 1×H$_2$O; C, 39.23%; H, 3.07%; N, 9.15%. Found: C, 39.41%; H, 2.79%; N, 9.15%.

Example 21

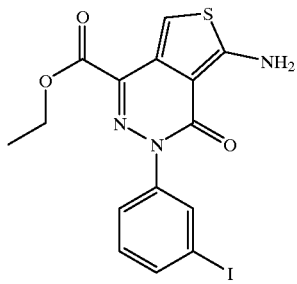

5-Amino-3-(3-iodo-phenyl)-4-oxo-3,4-dihydro-thieno[3,4-d]pyridazine-1-carboxylic acid ethyl ester M.p.: 186–187° C.;

Calculated for $C_{16}H_{12}IN_3O_3S$; C, 40.83%; H, 2.74%; N, 9.52%. Found: C, 40.76%; H, 2.71%; N, 9.54%.

Example 22

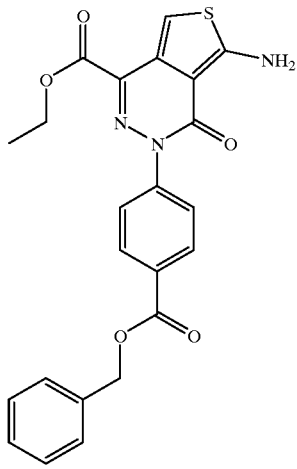

5-Amino-3-(4-benzyloxycarbonyl-phenyl)-4-oxo-3,4-dihydro-thieno[3,4-d]pyridazine-1-carboxylic acid ethyl ester M.p.: 130–133° C.

Calculated for $C_{23}H_{19}N_3O_5S$; C, 61.46%; H, 4.26%; N, 9.35%. Found: C, 61.24%; H, 4.04%; N, 9.37%.

Example 23

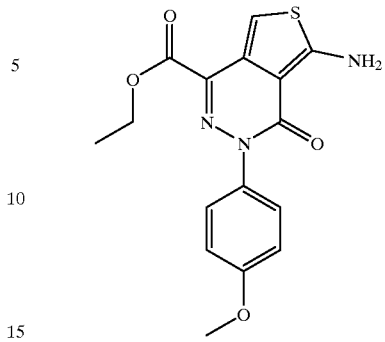

5-Amino-3-(4-methoxy-phenyl)-4-oxo-3,4-dihydro-thieno[3,4-d]pyridazine-1-carboxylic acid ethyl ester M.p.: 165–167° C.

Calculated for $C_{16}H_{15}N_3O_4S$; C, 55.64%; H, 4.38%; N, 12.17%. Found: C, 55.99%; H, 4.36%; N, 11.94%.

Example 24

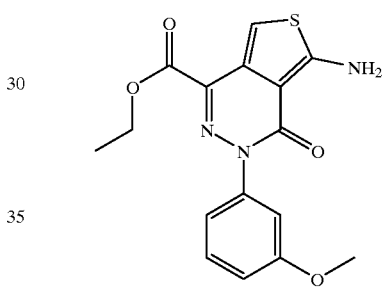

5-Amino-3-(3-methoxy-phenyl)-4-oxo-3,4-dihydro-thieno[3,4-d]pyridazine-1-carboxylic acid ethyl ester M.p.: 123–125° C.

Calculated for $C_{16}H_{15}N_3O_4S$, 0.25 $H_2O$; C, 54.93%; H, 4.47%; N, 12.01%. Found: C, 55.25%; H, 4.47%; N, 12.02%.

Example 25

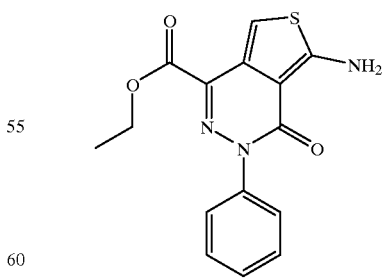

5-Amino-4-oxo-3-phenyl-3,4-dihydro-thieno[3,4-d]pyridazine-1-carboxylic acid ethyl ester Calculated for $C_{15}H_{13}N_3O_3S$; C, 57.13%; H, 4.16%; N, 13.32%. Found: C, 57.54%; H, 4.15%; N, 13.16%.

Example 26

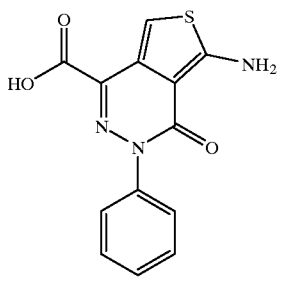

5-Amino-4-oxo-3-phenyl-3,4-dihydro-thieno[3,4-d]pyridazine-1-carboxylic acid

To a solution of the above pyridazine-1-carboxylic acid ethyl ester (3 g, 9.51 mmol) in a mixture of ethanol (50 ml) and water (25 ml) was added sodium hydroxide (0.46 g, 11.41 mmol). The resulting reaction mixture was stirred for 2.5 h at room temperature. Water (100 ml) was added, the aqueous phase was washed with ethyl acetate (50 ml), pH of the aqueous phase was adjusted to pH=3 by addition of concentrated hydrochloric acid. The precipitate was filtered off and washed with water (2×50 ml), heptane (2×50 ml) and dried in vacuo at 50° C. for 18 h affording 2.5 g (91%) of the title compound as a solid.

Calculated for $C_{13}H_9N_3O_3S$; C, 54.35%; H, 3.16%; N, 14.63%. Found: C, 57.52%; H, 3.29%; N, 14.23%.

Example 27

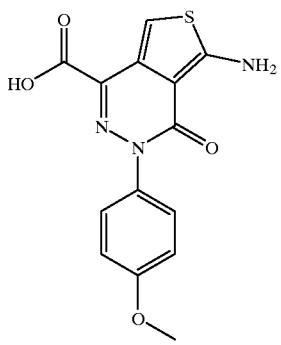

5-Amino-3-(3-methoxy-phenyl)-4-oxo-3,4-dihydro-thieno[3,4-d]pyridazine-1-carboxylic acid To a solution of 5-amino-3-(4-methoxy-phenyl)-4-oxo-3,4-dihydro-thieno[3,4-d]pyridazine-1-carboxylic acid ethyl ester (3 g, 8.69 mmol, prepared in example 23) in a mixture of ethanol (50 ml) and water (25 ml) was added sodium hydroxide (0.38 g, 9.55 mmol). The resulting reaction mixture was stirred for 2.5 h at room temperature. Water (150 ml) was added, undissolved matter was filtered off. The aqueous phase was washed with diethyl ether (2×100 ml), pH was adjusted to pH=4 by addition of concentrated hydrochloric acid. The precipitate was filtered off and washed with water (2×50 ml), heptane (2×50 ml) and dried in vacuo at 50° C. for 18 h affording 2.3 g (83%) of the title compound as a solid.

M.p.: 227–229° C.

Calculated for $C_{13}H_9N_3O_3S$, $0.25 \times H_2O$; C, 52.25%; H, 3.60%; N, 13.06%. Found: C, 52.43%; H, 3.54%; N, 12.94%.

The following compound was prepared in a similar way as described in example 2.

Example 28

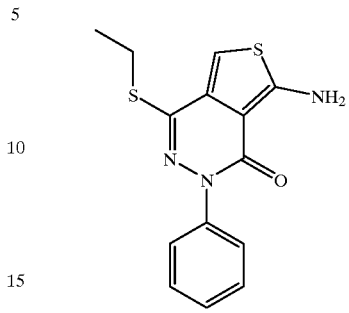

7-Amino-4-ethylsulfanyl-2-phenyl-thieno[3,4-d]pyridazin-1 (2H)-one

Calculated for $C_{14}H_{13}N_3OS_2$; C, 55.42%; H, 4.32%; N, 13.85%. Found: C, 55.46%; H, 4.40%; N, 13.73%.

Example 29

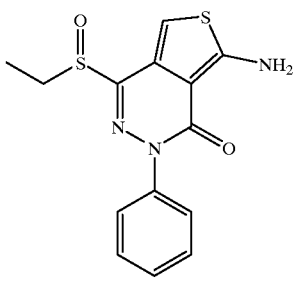

7-Amino-4-ethanesulfinyl-2-phenyl-2H-thieno[3,4-d]pyridazin-1-one

Aniline (20 g, 0.215 mol) was dissolved in a mixture of concentrated hydrochloric acid (64 ml) and water (64 ml). To the resulting mixture was added dropwise at 0° C. a solution of sodium nitrite (16.3 g, 0.24 mol) in water (80 ml). The resulting diazonium salt was added to a mixture of sodium acetate (53 g, 0.64 mol), ethanol (225 ml) and pentane-2,4-dione (21.5 g, 0.22 mol) at room temperature. The resulting mixture was stirred for 1 h at room temperature. The precipitate was filtered off and washed with water (2×150 ml), 50% aqueous ethanol (2×50 ml), heptane (50 ml) and dried in vacuo at 50° C. for 18 h affording 39.3 g (90%) of 3-(phenylhydrazono)-pentane-2,4-dione as a solid.

To a solution of the above hydrazon (20 g, 0.103 mol) in chloroform (75 ml) cooled in a ice bath was added dropwise t-butylhypochlorit (15 g, 0.103 mol). The resulting mixture was stirred at room temperature for 3 h. The volatiles were evaporated in vacuo affording crude 3-chloro-3-(phenylhydrazono)-pentane-2,4-dione as an oil.

The crude oil was dissolved in methanol (125 ml) and heated at reflux temperature for 5 min. The reaction mixture was cooled, the precipitate was filtered off, washed with a small portion of heptane and dried in vacuo at 50° C. for 18 h affording 10.3 g (51%) of pyruvoyl chloride 1-(phenyihydrazone) as a solid.

To a mixture of sodium ethoxide (100 ml; prepared from 1.2 g sodium and 100 ml ethanol) and ethyl mercaptane (4.1 ml, 0.055 mol) was added in small portion the above pyruvoyl chloride (10.3 g, 0.052 mol). The resulting mixture was stirred at room temperature for 66 h, diluted with water (200 ml) and extracted with diethyl ether (2×100 ml). The combined organic extracts were washed with water (2×100 ml), saturated aqueous sodium chloride (100 ml), dried (MgSO$_4$), filtered and evaporated in vacuo affording 11.1 g (95%) of 1-ethylsulfanyl-1,2-propanedione-1-(phenylhydrazone) as an oil.

A mixture of the above ethylsulfanyl (10.0 g, 0.045 mol), ethyl cyanoacetate (5.3 g, 0.047 mol) and ammonium acetate (6.9 g, 0.090 mol) was heated at reflux (105° C.) for 1.5 h. 75% aqueous ethanol (25 ml) was added at 60° C. and the resulting mixture was cooled to 10° C. The precipitate was filtered off and washed with water (4×50 ml), heptane (50 ml), a diethyl ether (25 ml) and dried in vacuo at 50° C. for 18 h affording 7.5 g (61%) of 6-ethylsulfanyl-5-methyl-3-oxo-2-phenyl-2,3-dihydro-pyridazine-4-carbonitrile as a solid.

The above pyridazine (1.5 g, 5.5 mmol) was dissolved in 40% peroxyacetic acid (30 ml) and the resulting mixture was stirred at room temperature for 18 h. Water (200 ml) was added and the precipitate was filtered off. The aqueous phase was extracted with ethyl acetate (2×100 ml), the combined organic phases were washed with water (3×100 ml), saturated aqueous sodium chloride (100 ml), dried (MgSO$_4$), filtered and evaporated in vacuo affording 1.3 g (82%) of 6-ethanesulfinyl-5-methyl-3-oxo-2-phenyl-2,3-dihydro-pyridazine-4-carbonitrile as a solid.

To a mixture of the above ethanesulfinyl pyridazine (1.1 g, 3.83 mmol) in ethanol (50 ml) was added sulfur (130 mg, 4.0 mmol) and morpholin (1 ml). The resulting mixture was heated at reflux temperature for 2 h. The reaction mixture was cooled and the volatiles were evaporated in vacuo. The residue was suspended in water (100 ml) and extracted with ethyl acetate (2×100 ml). The combined organic phases were washed with saturated aqueous sodium chloride (100 ml), dried (MgSO$_4$), filtered and evaporated in vacuo affording crude 0.65 g of the title compound which was purified on silica gel (500 ml) using a mixture of ethyl acetate and heptane (1:2) as eluent. Pure fractions were collected and the solvent evaporated in vacuo affording 0.5 g (41%) of the title compound as a solid.

M.p.: 204–205° C.

Calculated for C$_{14}$H$_{13}$N$_3$O$_2$S$_2$; C, 52.65%; H, 4.10%; N, 13.16%. Found: C, 52.75%; H, 4.14%; N, 12.94%.

Example 30

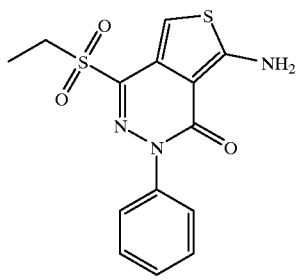

7-Amino-4-ethanesulfonyl-2-phenyl-2H-thieno[3,4-d]pyridazin-1-one

6-Ethanesulfinyl-5-methyl-3-oxo-2-phenyl-2,3-dihydro-pyridazine-4-carbonitrile (4.0 g, 15 mmol, prepared as described in example 29) was dissolved in 40% peroxyacetic acid (75 ml) and the resulting mixture was stirred at 60° C. for 4 h and at room temperature for 2 h. Water (300 ml) was added and the precipitate was filtered off. The aqueous phase was extracted with ethyl acetate (2×300 ml), the combined organic phases were washed with water (3×300 ml), saturated aqueous sodium chloride (100 ml), dried (MgSO$_4$), filtered and evaporated in vacuo affording 2.1 g of crude 6-ethanesulfinyl-5-methyl-3-oxo-2-phenyl-2,3-dihydro-pyridazine-4-carbonitrile. To the crude ethanesulfinyl (2.1 g) dissolved in dichloromethane (50 ml) was added 3-chloroperoxybenzoic acid (1.2 g) and the resulting reaction mixture was stirred at reflux temperature for 16 h. The cooled reaction was washed with water (50 ml), dried (MgSO$_4$), filtered and evaporated in vacuo which afforded crude 3.2 g. The crude product (3.2 g) was suspended in diethyl ether (50 ml), stirred for 2 h, filtered off, washed with diethyl ether (2×25 ml) and dried in vacuo at 50° C. affording 1.3 g (29%) of 6-ethanesulfonyl-5-methyl-3-oxo-2-phenyl-2,3-dihydro-pyridazine-4-carbonitrile as a solid. To a mixture of the above ethanesulfonyl pyridazine (0.5 g, 1.64 mmol) in ethanol (20 ml) was added sulfur (55 mg, 1.72 mmol) and morpholin (0.4 ml). The resulting mixture was heated at reflux temperature for 2 h. The reaction mixture was cooled and the precipitate was filtered off and washed with water (2×25 ml), heptane (25 ml) and dried in vacuo at 50° C. for 16 h affording 0.4 g (73%) of the title compound as a solid.

M.p.: 190–191° C.

Calculated for C$_{14}$H$_{13}$N$_3$O$_3$S$_2$; C, 50.14%; H, 3.91%; N, 12.53%. Found: C, 49.87%; H, 3.86%; N, 12.24%.

Example 31

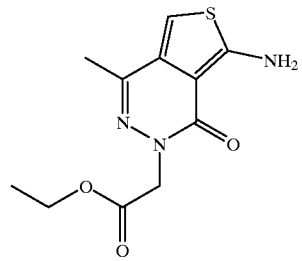

(7-Amino-4-methyl-1-oxo-1H-thieno[3,4-d]pyridazin-2-yl)acetic acid ethyl ester

To a solution of diacetyl (17.78 g, 0.20 mol) in water (300 ml) was added cyanoacetohydrazide (20.86 g, 0.20 mol). After stirring the resulting reaction mixture at room temperature for 2 h the precipitate was filtered off and washed with water (2×75 ml), a mixture of diethyl ether and ethanol (2×75 ml, 2:1) and dried in vacuo at 50° C. for 16 h which afforded 22.58 g (68%) of 2,3-butandione-2-(cyanoaetohydrazone) as a solid.

To a stirred solution of sodium ethoxide (350 ml, prepared from sodium hydride (18.17 g, 0.48 mol, 60% in mineral oil) and ethanol (350 ml) ) was added the above cyanoaetohydrazone (39.61 g, 0.24 mol) at 40° C. The resulting reaction mixture was heated at reflux temperature for 3 h, cooled to room temperature and poured onto ice (600 ml). pH of the solution was adjusted to pH=4 by addition of concentrated hydrochloric acid and the precipitate filtered off. The aqueous phase was evaporated in vacuo to ⅒ of its volume and the precipitate was filtered off. The combined filter cakes were washed with water (2×50 ml), a mixture of ethanol and diethyl ether (3×80 ml, 1:1) and dried in vacuo at 50° C. for 16 h which afforded 19.65 g (56%) of 5,6-dimethyl-3-oxo-2,3-dihydro-pyridazine-4-carbonitrile as a solid.

To a solution of the above pyridazine (5.0 g, 33.52 mmol) in dry dimethylsulfoxide (50 ml) was added sodium hydride (900 mg, 38.55 mmol, 60% in mineral oil) the reaction mixture was stirred at room temperature until gas evolution was ceased at which time at solution of bromo ethyl acetate (5.6 ml, 50.28 mmol) in dry dimethylsulfoxide (20 ml) was added dropwise. The reaction mixture was stirred at room temperature for 16 h, poured into a mixture of water (250 ml) and saturated aqueous sodium carbonate (50 ml) and extracted with dichloromethane (3×120 ml). The combined organic extracts were washed with water (100 ml), dried (MgSO4), filtered and evaporated in vacuo. The residue was treated with heptane (2×10 ml) and evaporated in vacuo at 60° C. which afforded 7.16 g (91%) of 6-cyano-4,5-dimethyl-1-oxo-pyridazin-2-yl)acetic acid ethyl ester as an oil.

TLC: $R_f$=0.41 (ethyl acetate/heptane 1:1)

$^1$H NMR (300 MHz, DMSO-d$_6$) $\delta_H$ 1.31 (t, 3H), 2.35 (s, 3H), 2.46 (s, 3H), 4.24 (q, 2H), 4.85 (s, 2H).

To a mixture of the above pyridazine (6.0 g, 25.5 mmol) in ethanol (20 ml) was added sulfur (860 mg, 26.8 mmol) and morpholin (5 ml). The resulting mixture was heated at 50° C. for 6 h. The reaction mixture was cooled and the precipitate was filtered off and washed with water (2×25 ml), heptane (25 ml) and dried in vacuo at 50° C. for 16 h affording 2.04 g (30%) of the title compound as a solid.

$^1$H NMR (300 MHz, DMSO-d$_6$) $\delta_H$ 1.20 (t, 3H), 2.21 (s, 3H), 4.12 (q, 2H), 4.60 (s, 2H), 6.70 (s, 1 H, thiophen), 7.35 (bs, 2H, NH$_2$).

Example 32

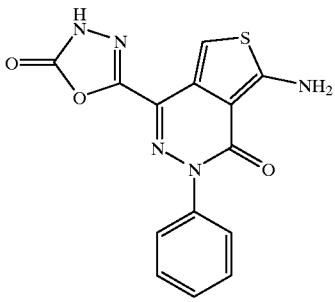

7-Amino-4-(5-oxo-4,5-dihydro[1,3,4]oxadiazol-2-yl)-2-phenyl-2H-thieno[3,4-d]pyridazin-1-one To a ice cooled solution of 5-amino-4-oxo-3-phenyl-3,4-dihydro-thieno[3,4-d]pyridazine-1-carboxylic acid hydrazide (2.0 g, 6.64 mmol), triethylamine (0.67 g, 6.64 mmol) in dry tetrahydrofuran (50 ml) was added 1,1'-carbonyidiimidazole (1.3 g, 8.30 mmol). The resulting reaction mixture was stirred at 0° C. for 1 h and at room temperature for 2 h. Water (100 ml) was added and the precipitate was filtered off and washed with water (2×25 ml), diethyl ether (20 ml) and dried in vacuo at 50° C. for 16 h affording 1.7 g (78%) of the title compound as a solid.

M.p.:>250° C.

Calculated for C$_{14}$H$_9$N$_5$O$_3$S; C, 50.00%; H, 3.00%; N, 20.82%. Found: C, 49.98%; H, 2.98%; N, 20.62%.

Example 33

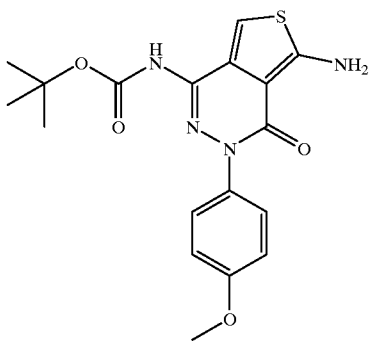

[5-Amino-3-(4-methoxy-phenyl)-4-oxo-3,4-dihydrothieno[3,4-d]pyridazin-1-yl]carbamic acid tert-butyl ester To a solution of 5-cyano-4-methyl-1-(4-methoxy-phenyl)-6-oxo-1,6-dihydro-pyridazine-3-carboxylic acid ethyl ester (15 g, 0.048 mol, prepared as described in example 23) in a mixture of ethanol (250 ml) and water (100 ml) was added sodium hydroxide (2.1 g, 0.053 mol). The reaction mixture was stirred at room temperature for 16 h, the volatiles were evaporated and the residue diluted with water (200 ml). The aqueous phase was washed with ethyl acetate (250 ml) and pH was adjusted to pH=2 by addition of concentrated hydrochloric acid. The precipitate was filtered off and washed with water (2×80 ml) and dried in vacuo at 50° C. for 16 h which afforded 12.3 g (90%) of 5-cyano-1-(4-methoxy-phenyl)-4-methyl-6-oxo-1,6-dihydro-pyridazine-3-carboxylic acid as a solid.

To a solution of the above carboxylic acid (5.0 g, 0.018 mol) in dry N,N-dimethylformamide (150 ml) was added triethylamine (2.1 g, 0.021 mol) and potassium tert-butoxide (1.6 g, 0.021 mol). The resulting mixture was cooled to 0° C. and diphenylphosphoryl azide (5.8 g, 0.021 mol) was added. Stirring was continued at 0° C. for 3 h and at room temperature for 16 h at which time water (300 ml) was added. The precipitate was filtered off and redissolved in ethyl acetate (250 ml) and filtered through a path of silica gel. The organic phase was washed with water (2×100 ml), saturated aqueous ammonium chloride (100 ml), dried (MgSO$_4$), filtered and evaporated in vacuo which afforded 2.2 g of the intermediate carboxylic acid azide (NMR). To a solution of potassium tert-butoxide (1.6 g) in tert-butanol (100 ml) was added the above crud carboxylic acid azide (2.2 g). The reaction mixture was stirred at reflux temperature for 16 h, the volatiles were evaporated in vacuo and the residue purified on silica gel (800 ml) using a mixture of ethyl acetate and heptane (1:1) as eluent. Pure fractions were collected and evaporated in vacuo affording 0.9 g (14 %) of [5-cyano-1-(4-methoxy-phenyl)-4-methyl-6-oxo-1,6-dihydro-pyridazin-3-yl]carbamic acid tert-butyl ester as a solid.

TLC: $R_f$=0.44 (ethyl acetatelheptane 1:1)

$^1$H NMR (300 MHz, CDCl$_3$) $\delta_H$ 1.51 (s, 9H), 2.53 (s, 3H), 3.87 (s, 3H), 6.47 (bs, 1 H, —OCONH—), 6.95 (d, 2H), 7.50 (d, 2H).

To a mixture of the above pyridazine (0.5 g, 1.4 mmol) in ethanol (30 ml) was added sulfur (43 mg, 1.5 mmol) and morpholin (0.5 ml). The resulting mixture was heated at 50° C. for 16 h. The volatiles were evaporated in vacuo, the residue was dissolved in ethyl acetate (100 ml) and washed with water (2×50 ml), dried (MgSO4), filtered and evaporated in vacuo. The residue 0.5 g was purified on silica gel (500 ml) using a mixture of ethyl acetate and heptane (1:1) as eluent. Pure fractions were collected and evaporated in vacuo affording 160 mg (29%) of the title compound as a solid.

M.p.: 99–101° C.

SP/MS(EI) Calculated 388.4, Found 388.1 (12%), 288.1 (48%).

$^1$H NMR (300 MHz, CDCl$_3$) $\delta_H$ 1.50 (s, 9H), 3.82 (s, 3H), 6.11 (bs, 2H, NH$_2$), 6.56 (bs, 1 H, —OCONH—), 6.93 (d, 2H), 7.24 (s, 1H, thiophen), 7.43 (d, 2H).

Example 34

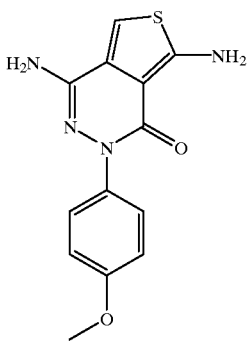

4,7-Diamino-2-(4-methoxy-phenyl)-2H-thieno[3,4-d]pyridazin-1-one

To a solution of [5-amino-3-(4-methoxy-phenyl)-4-oxo-3,4-dihydro-thieno[3,4-d]pyridazin-1-yl]carbamic acid tert-butyl ester (140 mg, 0.36 mmol, prepared as described in example 33) in dichloromethane (20 ml) was added trifluoroacetic acid (5 ml) and the reaction mixture was stirred at room temperature for 1 h. The volatiles were evaporated in vacuo and the residue was dissolved in ethanol and evaporated in vacuo. The semi solid residue was treated with diethyl ether (25 ml) for 16 h, the precipitate was filtered off and dried in vacuo at 50° C. for 16 h affording 30 mg crude title compound. The diethyl ether phase was evaporated and the residue was purified on silica gel (200 ml) using a mixture of ethyl acetate and heptane (3:1) as eluent. Pure fractions were collected and the solvent evaporated in vacuo affording 20 mg (19%) of the title compound as a solid.

SP/MS(EI) Calculated 288.4, Found 288.1 (100%).

$^1$H NMR (300 MHz, DMSO-d$_6$) $\delta_H$ 3.75 (s, 3H), 5.84 (bs, 2H, NH$_2$), 6.79 (s, 1H, thiophen), 6.90 (d, 2H), 7.35 (bs, 2H, NH$_2$), 7.39 (d, 2H).

What is claimed is:

1. A compound of Formula 1

Formula 1

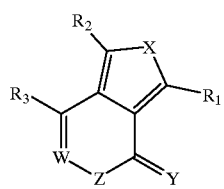

wherein

X is O, NH, S, SO or SO$_2$;

Y is or S;

R$_1$ is nitro, NH$_2$ or NHR$_4$ wherein R$_4$ is SO$_2$CF$_3$, C$_1$–C$_6$alkyl or arylC$_1$–C$_6$alkyl wherein aryl is phenyl or naphthyl, and the alkyl, phenyl and naphthyl groups are optionally substituted with COOR$_5$, C$_{1-6}$-alkyloxy, phenoxy, naphthyloxy, arylC$_{1-6}$-alkyloxy or halo, wherein R$_5$ is hydrogen, C$_{1-6}$-alkyl or arylC$_{1-6}$-alkyl wherein aryl is phenyl or napthyl;

R$_2$ is hydrogen, nitro, halo, cyano, C$_1$–C$_6$alkyl, aryl, arylC$_1$–C$_6$alkyl, COOR$_5$, carboxyC$_1$–C$_6$alkyl, C$_1$–C$_6$alkyloxycarbonyl, aryloxycarbonyl, arylC$_1$–C$_6$alkyl-oxycarbonyl or CONR$_6$R$_7$, wherein R$_5$, R$_6$ and R$_7$ are independently selected from hydrogen, hydroxy, C$_1$–C$_6$alkyl, aryl, arylC$_1$–C$_6$alkyl, C$_{1-6}$alkyl-carbonyl, arylcarbonyl, arylC$_1$–C$_6$alkylcarbonyl, C$_1$–C$_6$alkylcarboxy or arylC$_1$–C$_6$alkylcarboxy wherein aryl is phenyl or naphthyl, and the alkyl, phenyl and naphthyl groups are optionally substituted with COOR$_5$, C$_{1-6}$alkyloxy, phenoxy, naphthyloxy, arylC$_{1-6}$-alkyloxy or halo, wherein R$_5$ is hydrogen, C$_{1-6}$-alkyl or arylC$_{1-6}$-alkyl wherein aryl is phenyl or napthyl;

or R$_8$ and R$_7$ are independently a saturated or partially saturated cyclic 5, 6 or 7 membered amine or lactam;

R$_3$ is hydrogen, cyano, hydroxy, thiol, C$_1$–C$_6$alkylthio, SOC$_1$–C$_6$alkyl, SOC$_1$–C$_6$alkyl, COOR$_5$, C$_1$–C$_6$alkyl, C$_1$–C$_6$alkyloxy, NR$_6$R$_7$, aryl, arylC$_1$–C$_6$alkyl, C$_1$–C$_6$alkyloxycarbonylC$_1$–C$_6$alkyl, arylC$_1$–C$_6$alkyloxy-carbonylC$_1$–C$_6$alkyl, CONR$_6$R$_7$, -carbonylNR$_6$C$_1$–C$_6$alkylCOR$_8$; wherein aryl is phenyl or naphthyl and R$_8$ is hydroxy, C$_1$–C$_6$alkyl, aryl, arylC$_1$–C$_6$alkyl, C$_1$–C$_6$alkyloxy, aryloxy, arylC$_1$–C$_6$alkyloxy or NR$_6$R$_7$, wherein aryl is phenyl or naphthyl and R$_6$ and R$_7$ are defined as above; or R$_3$ is -C$_1$–C$_6$alkylCONR$_6$R$_7$, wherein R$_5$, R$_6$ and R$_7$ are defined as above; or R$_3$ is selected from

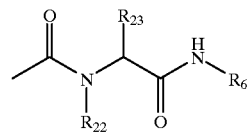

wherein R$_{22}$ and R$_{23}$ are independently hydrogen, C$_1$–C$_6$alkyl, aryl, arylC$_1$–C$_6$alkyl and R$_6$ is defined as above and aryl is phenyl or naphthyl, wherein the alkyl, phenyl and naphthyl groups are optionally substituted with COOR$_5$, C$_{1-6}$alkyloxy, phenoxy, naphthyloxy, arylC$_{1-6}$-alkyloxy or halo, wherein R$_5$ is hydrogen, C$_{1-6}$alkyl or arylC$_{1-6}$-alkyl wherein aryl is phenyl or napthyl;

W is N and Z is NR$_{11}$;

wherein R$_{11}$ is hydrogen, C$_1$–C$_6$alkyl, aryl, arylC$_1$–C$_6$alkyl, wherein aryl is phenyl or naphthyl, and the alkyl, phenyl and naphthyl groups are optionally substituted with COOR$_5$, C$_{1-6}$-alkyloxy, phenoxy, naphthyloxy, arylC$_{1-6}$-alkyloxy or halo, wherein R$_5$ is hydrogen, C$_{1-6}$-alkyl or arylC$_{1-6}$-alkyl wherein aryl is phenyl or napthyl; or $R_{11}$ is selected from

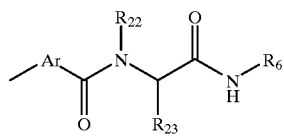

wherein Ar is phenyl or naphthyl and $R_6$, $R_{22}$ and $R_{23}$ are defined as above, wherein the phenyl and naphthyl groups are optionally substituted with $COOR_5$, $C_{1-6}$-alkyloxy, phenoxy, naphthyloxy, aryl$C_{1-6}$ alkyloxy or halo, wherein $R_5$ is hydrogen, $C_{1-6}$-alkyl or aryl$C_{1-6}$-akyl and aryl is phenyl or napthyl;

or a pharmaceutically acceptable salt thereof.

2. A compound of Formula 1

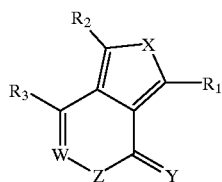

Formula 1 wherein

X is O, NH, S, SO or $SO_2$;

Y is O or S;

$R_1$ is nitro, $NH_2$ or $NHR_4$ wherein $R_4$ is $SO_2CF_3$, $C_1$–$C_6$alkyl or aryl$C_1$–$C_6$alkyl wherein aryl is phenyl or naphthyl, and the alkyl, phenyl and naphthyl groups are optionally substituted with halo, nitro, cyano, trihalomethyl, hydroxypyranyl, $C_1$–$C_6$alkyl, aryl$C_1$–$C_6$alkyl, hydroxy, carboxy, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkyl-thio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl $NR_6R_7$, $C_1$–$C_6$alkylamino$C_1$–$C_6$alkyl, aryl$C_1$–$C_6$alkylamino$C_1$–$C_6$alkyl, di(aryl$C_1$–$C_6$alkyl) amino$C_1$–$C_6$alkyl, $C_1$–$C_6$alkyl-carbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$alkyl, aryl$C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, -carbonyl$NR_6C_1$–$C_6$alkyl$COR_{15}$, aryl$C_1$–$C_6$alkylcarbonylamino, aryl$C_1$–$C_6$alkylcarbonylamino$C_1$–$C_6$alkyl, $CONR_6R_7$, $C_1$–$C_6$alkyl$CONR_6R_7$, or $C_1$–$C_6$alkyl$CONR_6R_7$ wherein aryl is phenyl or naphthyl and $R_{15}$ is $NR_6R_7$, or $C_1$–$C_6$alkyl$NR_6R_7$;

wherein $R_6$ and $R_7$ are independently selected from hydrogen, hydroxy, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein aryl is phenyl or naphthyl, and the alkyl, phenyl and naphthyl groups are optionally substituted with $COOR_5$, $C_{1-6}$-alkyloxy, phenoxy, naphthyloxy, aryl$C_{1-6}$-alkyloxy or halo, wherein $R_5$ is hydrogen, $C_{1-6}$-alkyl or aryl$C_{1-6}$-alkyl wherein aryl is phenyl or napthyl;

or $R_6$ and $R_7$ are independently a saturated or partially saturated cyclic 5, 6 or 7 membered amine or lactam;

$R_2$ is hydrogen, nitro, halo, cyano, $C_1$–$C_6$alkyl, aryl, aryl$C_1$–$C_6$alkyl, $COOR_5$, carboxy$C_1$–$C_6$alkyl, $C_1$–$C_6$alkyloxycarbonyl, aryloxycarbonyl, aryl$C_1$–$C_6$alkyloxycarbonyl or $CONR_6R_7$, wherein $R_5$, $R_6$ and $R_7$ are independently selected from hydrogen, hydroxy, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein aryl is phenyl or naphthyl, and the alkyl, phenyl and naphthyl groups are optionally substituted with $COOR_5$, $C_{1-6}$-alkyloxy, phenoxy, naphthyloxy, aryl$C_{1-6}$-alkyloxy or halo, wherein $R_5$ is hydrogen, $C_{1-6}$-alkyl or aryl$C_{1-6}$-alkyl wherein aryl is phenyl or napthyl;

or $R_6$ and $R_7$ are independently a saturated or partially saturated cyclic 5, 6 or 7 membered amine or lactam;

$R_3$ is hydrogen, cyano, hydroxy, thiol, $C_1$–$C_6$alkylthio, $SOC_1$–$C_6$alkyl, $SO_2C_1$–$C_6$alkyl, $COOR_5$, $C_1$–$C_6$alkyl, $C_1$–$C_6$alkyloxy, $NR_6R_7$, aryl, aryl$C_1$–$C_6$alkyl, $C_1$–$C_6$alkyloxycarbonyl$C_1$–$C_6$alkyl, aryl$C_1$–$C_6$alkyloxy-carbonyl$C_1$–$C_6$alkyl, $CONR_6R_7$, -carbonyl$NR_6C_1$–$C_6$alkyl$COR_8$; wherein aryl is phenyl or naphthyl and $R_8$ is hydroxy, $C_1$–$C_6$alkyl, aryl, aryl$C_1$–$C_6$alkyl, $C_1$–$C_6$alkyloxy, aryloxy, aryl$C_1$–$C_6$alkyloxy or $NR_6R_7$, wherein aryl is phenyl or naphthyl and $R_5$, $R_6$, and $R_7$ are defined as above; or $R_3$ is -$C_1$–$C_6$alkyl$CONR_6R_7$; or $R_3$ is selected from

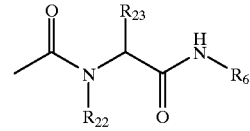

wherein $R_{22}$ and $R_{23}$ are independently hydrogen, $C_1$–$C_6$alkyl, aryl, aryl$C_1$–$C_6$alkyl and $R_6$ is defined as above and aryl is phenyl or naphthyl, wherein the alkyl, phenyl and naphthyl groups are unsubstituted or substituted with a member selected from the group consisting of $C_1$–$C_6$alkyl, aryl, aryl$C_1$–$C_6$alkyl, hydroxy, $C_1$–$C_6$alkyloxy, aryl$C_1$–$C_6$alkyloxy, $C_1$–$C_6$alkyloxy$C_1$–$C_6$alkyl, $NR_9R_{10}$ or $C_1$–$C_6$alkylamino$C_1$–$C_6$alkyl, wherein aryl is phenyl or naphthyl and $R_9$ and $R_{10}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein aryl is phenyl or naphthyl;

W is N and Z is $NR_{11}$;

wherein $R_{11}$ is hydrogen, $C_1$–$C_6$alkyl, aryl, aryl$C_1$–$C_6$alkyl, wherein aryl is phenyl or naphthyl, and the alkyl, phenyl and naphthyl groups are optionally substituted with $COOR_5$, $C_{1-6}$-alkyloxy, phenoxy, naphthyloxy, aryl$C_{1-6}$-alkyloxy or halo, wherein $R_5$ is hydrogen, $C_{1-6}$-alkyl or aryl$C_{1-6}$-alkyl wherein aryl is phenyl or napthyl; or

47

$R_{11}$ is selected from

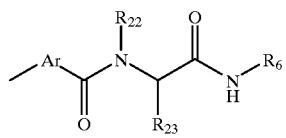

wherein Ar is phenyl or naphthyl and $R_6$, $R_{22}$ and $R_{23}$ are defined as above and wherein the alkyl, phenyl and naphthyl groups are unsubstituted or substituted with a member selected from the group consisting of $C_1$–$C_6$alkyl, aryl, aryl$C_1$–$C_6$alkyl, hydroxy, $C_1$–$C_6$alkyloxy, aryl$C_1$–$C_6$alkyloxy, $C_1$–$C_6$alkyloxy$C_1$–$C_6$alkyl, $NR_9R_{10}$ or $C_1$–$C_6$alkylamino$C_1$–$C_6$alkyl, wherein aryl is phenyl or naphthyl and $R_9$ and $R_{10}$ are independently selected from hydrogen, $C_1$–$C_6$alkyl, aryl, aryl$C_1$–$C_6$alkyl, $C_1$–$C_6$alkyl-carbonyl, arylcarbonyl, aryl$C_1$–$C_6$alkylcarbonyl, $C_1$–$C_6$alkyl-carboxy or aryl$C_1$–$C_6$alkylcarboxy wherein aryl is phenyl or naphthyl;
or a pharmaceutically acceptable salt thereof.

3. A compound according to claim 1, wherein $R_{11}$ is aryl or substituted aryl.

4. A compound according to claim 1, wherein $R_3$ is $COOR_5$, $CONR_6R_7$; or $R_3$ is selected from

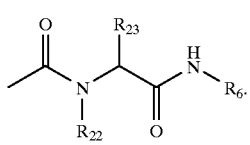

5. A compound according to claim 1, wherein $R_{11}$ is phenyl substituted with —COOH.

6. A compound according to claim 1, wherein $R_{11}$ is phenyl substituted with $COOR_5$, $CONR_6R_7$ or

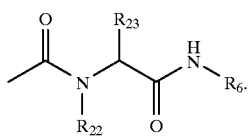

7. A compound according to claim 1, wherein the pharmaceutically acceptable salt is a morpholin salt.

8. A compound selected from the following:

5-Amino-3-(4-methoxy-phenyl)-4-oxo-3,4-dihydro-thieno[3,4-d]pyridazine-1-carboxylic acid ethyl ester;

7-Amino4-ethylsulfanyl-2-(4-methoxy-phenyl)thieno[3,4-d]pyridazin-1(2H)-one;

5-Amino-3-(4-carboxy-phenyl)-4-oxo-3,4-dihydro-thieno[3,4-d]pyridazine-1-carboxylic acid ethyl ester;

7-Amino4-ethylsulfanyl-2-phenyl-thieno[3,4-d]pyridazin-1 (2H)-one;

5-Amino-3-(3-carboxy-phenyl)-4-oxo-3,4-dihydro-thieno[3,4-d]pyridazine-1- carboxylic acid ethyl ester;

5-Amino-4-oxo-3-phenyl-3,4-dihydro-thieno[3,4-d]pyridazine-1-carbothioic acid amide;

7-Amino-4-cyano-2-(2-methoxy-phenyl)-1-oxo-1,2-dihydro-thieno[3,4-d]pyridazine-5-carboxylic acid ethyl ester;

48

5-Amino-4-oxo-3-phenyl-3,4-dihydro-thieno[3,4-d]pyridazine-1-carbonitrile;

5-Amino-4-oxo-3-phenyl-3,4-dihydro-thieno[3,4-d]pyridazine-1-carboxylic acid hydrazide;

5-Amino-4-oxo-3-phenyl-3,4-dihydro-thieno[3,4-d]pyridazine-1-carboxylic acid ethyl ester;

5-Amino-4-oxo-3-phenyl-3,4-dihydro-thieno[3,4-d]pyridazine-1-carboxylic acid;

5-Amino-3-(3-methoxy-phenyl)-4-oxo-3,4-dihydro-thieno[d]pyridazine-1-carboxylic acid ethyl ester;

5-Amino-3-(4-((1-benzylcarbamoyl-pentyl)isopropyl-carbamoyl)phenyl)-4-oxo-3,4-dihydro-thieno[3,4-d]pyridazine-1-carboxylic acid ethyl ester;

5-Amino-3-(4-((1-benzylcarbamoyl-pentylcarbamoyl)phenyl)-4-oxo-3,4-dihydro-thieno[3,4-d]pyridazine-1-carboxylic acid ethyl ester;

5-Amino-3-(4-((1-(5-carboxy-pentylcarbamoyl)-pentyl)isopropyl-carbamoyl)phenyl)-4-oxo-3,4-dihydro-thieno[3,4-d]pyridazine-1-carboxylic acid ethyl ester;

5-Amino-3-(4-chloro-phenyl)-4-oxo-3,4-dihydro-thieno[3,4-d]pyridazine-1-carboxylic acid ethyl ester;

5-Amino-7-bromo-4-oxo-3-phenyl-3,4-dihydro-thieno[3,4-d]pyridazine-1-carboxylic acid ethyl ester;

5-Amino-3-(4-iodo-phenyl)-4-oxo-3,4-dihydro-thieno[3,4-d]pyridazine-1-carboxylic acid ethyl ester;

5-Amino-3-(3-iodo-phenyl)-4-oxo-3,4-dihydro-thieno[3,4-d]pyridazine-1-carboxylic acid ethyl ester;

5-Amino-3-(4-benzyloxycarbonyl-phenyl)-4-oxo-3,4-dihydro-thieno(3,4-d)pyridazine-1-carboxylic acid ethyl ester;

5-Amino-3-(3-methoxy-phenyl)-4-oxo-3,4-dihydro-thieno[3,4-d]pyridazine-1-carboxylic acid;

7-Amino-4-ethanesulfinyl-2-phenyl-2H-thieno[3,4-d]pyridazin-1-one;

7-Amino4-ethanesulfonyl-2-phenyl-2H-thieno[3,4-d]pyridazin-1-one;

(7-Amino-4-methyl-1-oxo-1H-thieno[3,4-d]pyridazin-2-yl)acetic acid ethyl ester;

7-Amino-4-(5-oxo4,5-dihydro[3,4]oxadiazol-2-yl)-2-phenyl-2H-thieno[3,4-d]pyridazin-1-one;

[5-Amino-3-(4-methoxy-phenyl)-4-oxo-3,4-dihydo-thieno[3,4-d]dipyridazin-1-yl]carbamic acid tert-butyl ester;

4,7-Diamino-2-(4-methoxy-phenyl)-2H-thieno[3,4-d]pyridazin-1-one;

or a pharmaceutically acceptable salt thereof.

9. Compounds according to claim 1 which act as inhibitors of Protein Tyrosine Phosphatases.

10. A pharmaceutical composition comprising a compound according to claim 1 together with one or more pharmaceutically acceptable carriers or diluents.

11. The pharmaceutical composition according to claim 10 in the form of an oral dosage unit or parenteral dosage unit.

12. The pharmaceutical composition according to claim 10, wherein said compound is administered as a dose in a range from about 0.05 to 1000 mg per day.

13. The pharmaceutical composition according to claim 12, wherein said compound is administered as a dose in a range from about 0.1 to 500 mg per day.

14. The pharmaceutical composition according to claim 13, wherein said compound is administered as a dose in a range from about 50 to 200 mg per day.

15. A method of treating type I diabetes, type II diabetes, impaired glucose tolerance, insulin resistance, obesity, immune dysfunctions including autoimmunity, diseases with dysfunctions of the coagulation system, allergic diseases, cancer and psoriasis, diseases with decreased or increased synthesis or effects of growth hormone, diseases with decreased or increased synthesis of hormones or cytokines that regulate the release of/or response to growth hormone, the method comprising administering to a subject in need thereof a therapeutically effective amount of a compound according to claim 1.

16. A method of treating type I diabetes, type II diabetes, impaired glucose tolerance, insulin resistance and obesity, the method comprising administering to a subject in need thereof a therapeutically effective amount of a compound according to claim 1.

17. A method of treating diseases with dysfunctions of the coagulation system, the method comprising administering to a subject in need thereof a therapeutically effective amount of a compound according to claim 1.

18. A method of treating allergic diseases, the method comprising administering to a subject in need thereof a therapeutically effective amount of a compound according to claim 1.

19. A method of treating cancer and psoriasis, the method comprising administering to a subject in need thereof a therapeutically effective amount of a compound according to claim 1.

20. A method of treating diseases with decreased or increased synthesis or effects of growth hormone and diseases with decreased or increased synthesis of hormones or cytokines that regulate the release of/or response to growth hormone, the method comprising administering to a subject in need thereof a therapeutically effective amount of a compound according to claim 1.

* * * * *